US008864650B2

(12) United States Patent
Inman et al.

(10) Patent No.: US 8,864,650 B2
(45) Date of Patent: Oct. 21, 2014

(54) METHODS AND APPARATUS FOR SECURING A URETHRAL SLING TO A PUBIC BONE

(75) Inventors: Mona J. Inman, Eden Prairie, MN (US); Kevin R. Arnal, Excelsior, MN (US); Matthew J. Monarski, Victoria, MN (US); Robert L. Rykhus, Jr., Edina, MN (US); Suranjan Roychowdhury, Plymouth, MN (US); Jeffrey A. Lechner-Riehle, Burnsville, MN (US); Eric S. Watschke, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 2038 days.

(21) Appl. No.: 11/993,397

(22) PCT Filed: Jun. 20, 2006

(86) PCT No.: PCT/US2006/023871
§ 371 (c)(1),
(2), (4) Date: Mar. 10, 2010

(87) PCT Pub. No.: WO2007/002012
PCT Pub. Date: Jan. 4, 2007

(65) Prior Publication Data
US 2010/0168505 A1   Jul. 1, 2010

Related U.S. Application Data

(60) Provisional application No. 60/692,662, filed on Jun. 21, 2005.

(51) Int. Cl.
*A61F 2/00* (2006.01)
*A61B 17/04* (2006.01)
*A61B 17/88* (2006.01)
*A61B 17/00* (2006.01)
*A61B 17/064* (2006.01)

(52) U.S. Cl.
CPC ........... *A61F 2/0045* (2013.01); *A61B 17/0401* (2013.01); *A61B 2017/0496* (2013.01);
(Continued)

(58) Field of Classification Search
USPC ........ 600/29–32, 37; 606/151, 300, 301, 289, 606/290
See application file for complete search history.

(56) References Cited

U.S. PATENT DOCUMENTS

| 2,738,790 | A | 3/1956 | Todt et al. |
| 3,472,232 | A | 10/1969 | Earl |

(Continued)

FOREIGN PATENT DOCUMENTS

| AU | 2002241673 | 11/2005 |
| CA | 2404459 | 8/2005 |

(Continued)

OTHER PUBLICATIONS

"We're staying ahead of the curve" Introducing the IVS Tunneller Device for Tension Free Procedures, Tyco Healthcare, 3 pages (2002).

(Continued)

*Primary Examiner* — Charles A Marmor, II
*Assistant Examiner* — Carrie R Dorna
(74) *Attorney, Agent, or Firm* — Kagan Binder, PLLC

(57) ABSTRACT

Surgical procedures, kits and implants for alleviating human incontinence, and particularly providing improved methods and apparatus to secure a urethral sling to pubic bone in a sub-urethral location to support the urethra and alleviate incontinence are disclosed. Bone anchors, e.g., bone screws, are driven into pubic bones with exposed bone anchor heads and necks configured to receive and support a urethral sling applied to the bone anchors with and without retainers applied against the urethral sling to retain portions of the urethral sling between the bone anchor heads and the pubic bones.

19 Claims, 18 Drawing Sheets

(52) U.S. Cl.
CPC .. *A61B 2017/045* (2013.01); *A61B 2017/0414* (2013.01); *A61B 2017/00805* (2013.01); *A61B 2017/00734* (2013.01); *A61B 2017/044* (2013.01); *A61B 2017/0454* (2013.01); *A61B 17/0487* (2013.01); A61B 17/8875 (2013.01); *A61B 2017/0409* (2013.01); *A61B 17/064* (2013.01); *A61B 17/0643* (2013.01)
USPC .............................. 600/37; 600/30; 606/151

(56) References Cited

U.S. PATENT DOCUMENTS

| | | | |
|---|---|---|---|
| 3,580,313 A | 5/1971 | McKnight | |
| 3,763,860 A | 10/1973 | Clarke | |
| 3,858,783 A | 1/1975 | Kapitanov et al. | |
| 3,995,619 A | 12/1976 | Glatzer | |
| 4,172,458 A | 10/1979 | Pereyra | |
| 4,235,238 A | 11/1980 | Ogiu et al. | |
| 4,441,497 A | 4/1984 | Paudler | |
| 4,509,516 A | 4/1985 | Richmond | |
| 4,548,202 A | 10/1985 | Duncan | |
| 4,632,100 A | 12/1986 | Somers et al. | |
| 4,873,976 A | 10/1989 | Schreiber | |
| 4,932,962 A | 6/1990 | Yoon et al. | |
| 4,938,760 A | 7/1990 | Burton et al. | |
| 4,969,892 A | 11/1990 | Burton et al. | |
| 4,979,956 A | 12/1990 | Silvestrini | |
| 5,013,292 A | 5/1991 | Lemay | |
| 5,013,316 A | 5/1991 | Goble et al. | |
| 5,053,043 A | 10/1991 | Gottesman et al. | |
| 5,085,661 A | 2/1992 | Moss | |
| 5,112,344 A | 5/1992 | Petros | |
| 5,141,520 A | 8/1992 | Goble et al. | |
| 5,149,329 A | 9/1992 | Richardson | |
| 5,188,636 A | 2/1993 | Fedotov | |
| 5,209,756 A | 5/1993 | Seedhom et al. | |
| 5,234,438 A | 8/1993 | Semrad | |
| 5,256,133 A | 10/1993 | Spitz | |
| 5,268,001 A | 12/1993 | Nicholson et al. | |
| 5,269,783 A | 12/1993 | Sander | |
| 5,281,237 A | 1/1994 | Gimpelson | |
| 5,328,077 A | 7/1994 | Lou | |
| 5,337,736 A | 8/1994 | Reddy | |
| 5,354,292 A | 10/1994 | Braeuer et al. | |
| 5,368,595 A | 11/1994 | Lewis | |
| 5,370,650 A | 12/1994 | Tovey et al. | |
| 5,370,662 A | 12/1994 | Stone et al. | |
| 5,376,097 A | 12/1994 | Phillips | |
| 5,383,904 A | 1/1995 | Totakura et al. | |
| 5,403,328 A | 4/1995 | Shallman | |
| 5,439,467 A | 8/1995 | Benderev et al. | |
| 5,474,518 A | 12/1995 | Velazquez | |
| 5,474,543 A | 12/1995 | McKay | |
| 5,520,700 A | 5/1996 | Beyar et al. | |
| 5,520,703 A | 5/1996 | Essig | |
| 5,527,342 A | 6/1996 | Pietrzak et al. | |
| 5,544,664 A | 8/1996 | Benderev et al. | |
| 5,562,689 A | 10/1996 | Green et al. | |
| 5,571,139 A | 11/1996 | Jenkins, Jr. | |
| 5,582,188 A | 12/1996 | Benderev et al. | |
| 5,591,163 A | 1/1997 | Thompson | |
| 5,591,206 A | 1/1997 | Moufarrege | |
| 5,611,515 A | 3/1997 | Benderev et al. | |
| 5,628,756 A | 5/1997 | Barker, Jr. et al. | |
| 5,643,320 A | 7/1997 | Lower et al. | |
| 5,669,935 A | 9/1997 | Rosenman et al. | |
| 5,683,349 A | 11/1997 | Makower et al. | |
| 5,690,655 A | 11/1997 | Hart et al. | |
| 5,697,931 A | 12/1997 | Thompson | |
| 5,709,708 A | 1/1998 | Thal | |
| 5,725,529 A | 3/1998 | Nicholson et al. | |
| 5,725,541 A | 3/1998 | Anspach, III et al. | |
| 5,741,282 A | 4/1998 | Anspach, III et al. | |
| 5,842,478 A | 12/1998 | Benderev et al. | |
| 5,899,909 A | 5/1999 | Claren et al. | |
| 5,904,692 A | 5/1999 | Steckel et al. | |
| 5,922,026 A | 7/1999 | Chin | |
| 5,925,047 A | 7/1999 | Errico et al. | |
| 5,944,732 A | 8/1999 | Raulerson et al. | |
| 5,954,057 A | 9/1999 | Li | |
| 5,972,000 A | 10/1999 | Beyar et al. | |
| 5,980,558 A | 11/1999 | Wiley | |
| 5,984,927 A | 11/1999 | Wenstrom, Jr. | |
| 5,988,171 A | 11/1999 | Sohn et al. | |
| 5,997,554 A | 12/1999 | Thompson | |
| 6,027,523 A | 2/2000 | Schmieding | |
| 6,030,393 A | 2/2000 | Corlew | |
| 6,036,701 A | 3/2000 | Rosenman | |
| 6,042,583 A | 3/2000 | Thompson et al. | |
| 6,048,351 A | 4/2000 | Gordon et al. | |
| 6,053,935 A | 4/2000 | Brenneman et al. | |
| 6,056,688 A | 5/2000 | Benderev et al. | |
| 6,099,538 A | 8/2000 | Moses | |
| 6,127,597 A | 10/2000 | Beyar et al. | |
| 6,168,611 B1 | 1/2001 | Risvi | |
| 6,200,330 B1 | 3/2001 | Benderev et al. | |
| 6,241,736 B1 | 6/2001 | Sater et al. | |
| 6,245,082 B1 | 6/2001 | Gellman et al. | |
| 6,264,676 B1 | 7/2001 | Gellman et al. | |
| 6,273,852 B1 | 8/2001 | Lehe et al. | |
| 6,322,492 B1 | 11/2001 | Kovac | |
| 6,328,744 B1 | 12/2001 | Harari et al. | |
| 6,334,446 B1 | 1/2002 | Beyar | |
| 6,382,214 B1 | 5/2002 | Raz et al. | |
| 6,387,041 B1 | 5/2002 | Harari et al. | |
| 6,406,423 B1 | 6/2002 | Scetbon | |
| 6,406,480 B1 | 6/2002 | Beyar et al. | |
| 6,423,080 B1 | 7/2002 | Gellman et al. | |
| 6,451,024 B1 | 9/2002 | Thompson et al. | |
| 6,475,139 B1 | 11/2002 | Miller | |
| 6,478,727 B2 | 11/2002 | Scetbon | |
| 6,491,703 B1 | 12/2002 | Ulmsten | |
| 6,502,578 B2 | 1/2003 | Raz et al. | |
| 6,506,190 B1 | 1/2003 | Walshe | |
| 6,530,943 B1 | 3/2003 | Hoepffner et al. | |
| 6,544,273 B1 | 4/2003 | Harari et al. | |
| 6,575,987 B2 * | 6/2003 | Gellman et al. | 606/151 |
| 6,582,443 B2 | 6/2003 | Cabak et al. | |
| 6,592,515 B2 | 7/2003 | Thierfelder | |
| 6,592,610 B2 | 7/2003 | Beyar | |
| 6,596,001 B2 | 7/2003 | Stormby et al. | |
| 6,599,235 B2 | 7/2003 | Kovac | |
| 6,602,260 B2 | 8/2003 | Harari et al. | |
| 6,612,977 B2 | 9/2003 | Staskin | |
| 6,635,058 B2 | 10/2003 | Beyar et al. | |
| 6,638,210 B2 | 10/2003 | Berger | |
| 6,641,525 B2 | 11/2003 | Rocheleau | |
| 6,673,010 B2 | 1/2004 | Skiba et al. | |
| 6,685,629 B2 | 2/2004 | Therin | |
| 6,689,047 B2 | 2/2004 | Gellman et al. | |
| 6,730,110 B1 | 5/2004 | Harari et al. | |
| 6,746,455 B2 | 6/2004 | Beyar et al. | |
| 6,752,814 B2 | 6/2004 | Gellman et al. | |
| 6,802,807 B2 | 10/2004 | Anderson | |
| 6,884,212 B2 | 4/2005 | Thierfelder et al. | |
| 6,908,425 B2 | 6/2005 | Luscombe | |
| 6,908,473 B2 | 6/2005 | Skiba et al. | |
| 6,911,002 B2 | 6/2005 | Fierro | |
| 6,911,003 B2 | 6/2005 | Anderson et al. | |
| 6,932,759 B2 | 8/2005 | Kammerer | |
| 6,936,052 B2 | 8/2005 | Gellman et al. | |
| 6,971,986 B2 | 12/2005 | Staskin et al. | |
| 6,974,462 B2 | 12/2005 | Sater | |
| 6,981,983 B1 | 1/2006 | Rosenblatt et al. | |
| 6,991,597 B2 | 1/2006 | Gellman et al. | |
| 7,014,607 B2 | 3/2006 | Gellman | |
| 7,025,772 B2 | 4/2006 | Gellman et al. | |
| 7,037,255 B2 | 5/2006 | Inman | |
| 7,048,682 B2 | 5/2006 | Neisz et al. | |
| 7,056,333 B2 | 6/2006 | Walshe | |
| 7,070,556 B2 | 7/2006 | Anderson | |
| 7,083,637 B1 | 8/2006 | Tannhauser | |
| 7,087,059 B2 | 8/2006 | Harari et al. | |
| 7,112,171 B2 | 9/2006 | Rocheleau et al. | |

(56) References Cited

U.S. PATENT DOCUMENTS

| | | |
|---|---|---|
| 7,121,997 B2 | 10/2006 | Kammerer et al. |
| 7,131,943 B2 | 11/2006 | Kammerer |
| 7,223,229 B2 | 5/2007 | Inman et al. |
| 7,226,407 B2 | 6/2007 | Kammerer |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,267,645 B2 | 9/2007 | Anderson |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,494,495 B2 | 2/2009 | Delorme et al. |
| 7,500,945 B2 | 3/2009 | Cox |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Priewe et al. |
| 7,588,598 B2 | 9/2009 | Delorme et al. |
| 7,601,118 B2 | 10/2009 | Smith et al. |
| 7,614,999 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |
| 7,691,052 B2 | 4/2010 | Gellman et al. |
| 7,740,576 B2 | 6/2010 | Hodroff |
| 7,753,839 B2 | 7/2010 | Siegel et al. |
| 7,762,942 B2 | 7/2010 | Neisz et al. |
| 2001/0018549 A1 | 8/2001 | Scetbon |
| 2001/0041895 A1 | 11/2001 | Beyer et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1 | 3/2002 | Thierfelder et al. |
| 2002/0055748 A1 | 5/2002 | Gellman et al. |
| 2002/0058959 A1 | 5/2002 | Gellman et al. |
| 2002/0068948 A1 | 6/2002 | Stormby et al. |
| 2002/0077526 A1 | 6/2002 | Kammerer et al. |
| 2002/0077631 A1* | 6/2002 | Lubbers et al. ............... 606/72 |
| 2002/0082619 A1 | 6/2002 | Cabak et al. |
| 2002/0091373 A1 | 7/2002 | Berger |
| 2002/0095163 A1 | 7/2002 | Beyer et al. |
| 2002/0107525 A1 | 8/2002 | Harari et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0193215 A1 | 9/2004 | Harari et al. |
| 2004/0225181 A1 | 11/2004 | Chu et al. |
| 2004/0267088 A1 | 12/2004 | Krammerer |
| 2005/0000523 A1 | 1/2005 | Beraud |
| 2005/0004576 A1 | 1/2005 | Benderev |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0195007 A1 | 8/2006 | Anderson |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0078295 A1 | 4/2007 | Landgrebe |
| 2007/0173864 A1 | 7/2007 | Chu |
| 2008/0039678 A1 | 2/2008 | Montpetit et al. |
| 2008/0300607 A1 | 12/2008 | Meade et al. |
| 2009/0012353 A1 | 1/2009 | Beyer |
| 2009/0221867 A1 | 9/2009 | Ogdahl et al. |
| 2009/0221868 A1 | 9/2009 | Evans |

FOREIGN PATENT DOCUMENTS

| | | |
|---|---|---|
| DE | 2305815 | 2/1973 |
| DE | 4220283 C2 | 5/1994 |
| DE | 10211360 | 9/2003 |
| DE | 20016866 | 3/2007 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1342450 B1 | 9/2003 |
| FR | 2852813 A1 | 1/2004 |
| GB | 2268690 A | 1/1994 |
| GB | 2353220 A | 10/2000 |
| SU | 1225547 A1 | 4/1986 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9842261 A1 | 10/1998 |
| WO | WO9853746 A1 | 12/1998 |
| WO | WO9938217 A1 | 7/1999 |
| WO | WO9952450 A1 | 10/1999 |
| WO | WO9953844 A1 | 10/1999 |
| WO | WO9959477 A1 | 11/1999 |
| WO | WO0013601 A1 | 3/2000 |
| WO | WO0040158 A2 | 7/2000 |
| WO | WO0074594 A1 | 12/2000 |
| WO | WO0074613 A1 | 12/2000 |
| WO | WO0074633 A2 | 12/2000 |
| WO | WO0230293 A1 | 4/2002 |
| WO | WO0232284 A2 | 4/2002 |
| WO | WO0234124 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO03013392 A2 | 2/2003 |
| WO | WO03017848 A1 | 3/2003 |
| WO | WO03047435 A1 | 6/2003 |
| WO | WO03067107 A1 | 8/2003 |
| WO | WO03075792 A1 | 9/2003 |
| WO | WO03086205 A2 | 10/2003 |

(56) References Cited

FOREIGN PATENT DOCUMENTS

| WO | WO03092546 | A2 | 11/2003 |
|---|---|---|---|
| WO | WO03096928 | A1 | 11/2003 |
| WO | WO03096929 | A1 | 11/2003 |
| WO | WO2004016196 | A2 | 2/2004 |
| WO | WO2004034912 | A1 | 4/2004 |
| WO | WO2005004727 | A1 | 1/2005 |
| WO | WO2005046511 | A2 | 5/2005 |
| WO | WO2005048850 | A2 | 6/2005 |
| WO | WO2005079702 | A1 | 9/2005 |
| WO | WO2005122954 | A1 | 12/2005 |
| WO | WO2006007189 | A1 | 1/2006 |
| WO | WO2006007190 | A1 | 1/2006 |
| WO | WO2006031879 | A1 | 3/2006 |
| WO | WO2006108145 | A1 | 10/2006 |
| WO | WO2007002012 | A1 | 1/2007 |
| WO | WO2007002071 | A1 | 1/2007 |
| WO | WO2007014241 | A2 | 2/2007 |
| WO | WO2007016083 | A1 | 2/2007 |
| WO | WO2007027592 | A2 | 3/2007 |
| WO | WO2007059199 | A2 | 5/2007 |
| WO | WO2007097994 | | 8/2007 |
| WO | WO2007137226 | A2 | 11/2007 |
| WO | WO2007146784 | A2 | 12/2007 |
| WO | WO2007149348 | A2 | 12/2007 |
| WO | WO2008057261 | A2 | 5/2008 |
| WO | WO2008124056 | A1 | 10/2008 |
| WO | WO2009005714 | A2 | 1/2009 |
| WO | WO2009017680 | A2 | 2/2009 |

OTHER PUBLICATIONS

Advantage A/T™, Surgical Mesh Sling Kit, Boston Scientific, 6 pages (2002).
Benderev, Theodore V., MD, A Modified, Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, 409-418 (Nov. 1992).
Capio™ CL—Transvaginal Suture Capturing Device—Transvaginal Suture Fixation to Cooper's Ligament for Sling Procedures, Boston Scientific, Microvasive®, 8 pages, (2002).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Gynecare TVT Tension-Free Support for Incontinence, The tension-free solution to female Incontinence, Gynecare Worldwide, 6 pages, (2002).
IVS Tunneller—A Universal instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages (2001).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kovac, S. Robert, et al, Pubic Bone Suburethral Stabilization Sling: A Long Term Cure for SUI?, Contemporary OB/GYN, 10 pages (Feb. 1998).
Sabre™ Bioabsorbable Sling, Generation Now, Mentor, 4 pages (May 2002).
Sabre™ Surgical Procedure, Mentor, 6 pages (Aug. 2002).
Sanz, Luis E. et al., Modification of Abdominal Sacrocolpopexy Using a Suture System, The Journal of Reproductive Anchor Medicine, vol. 48, n. 7, pp. 496-500 (Jul. 2003).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, Ulf et al., A Three Year of Follow Up of Tension Free Vaginal Tape for Surgical Treatment of Female Stress Urinary Incontinence, British Journal of Obstetrics and Gynaecology, vol. 106, pp. 345-350 (1999).
Vesica® Percutaneous Bladder Neck Stabilization Kit, A New Approach to Bladder Neck Suspenison, Microvasive® Boston Scientific Corporation, 4 pages (1995).

\* cited by examiner

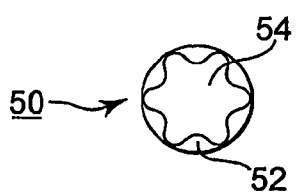
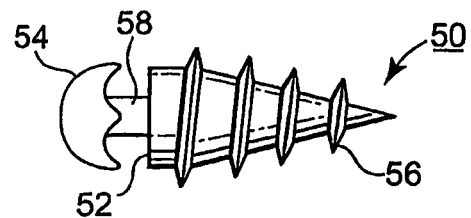
Fig. 4A     Fig. 4B
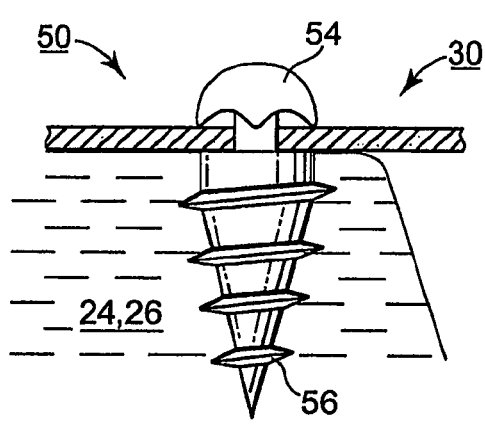
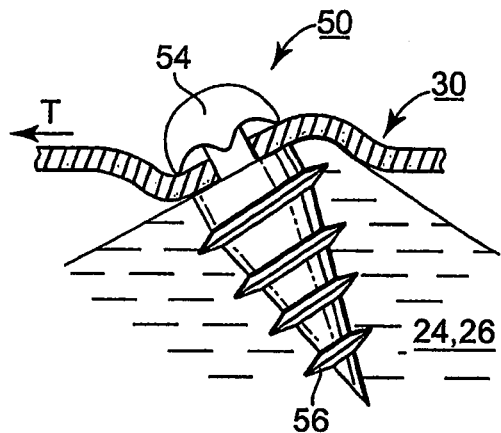
Fig. 4C     Fig. 4D
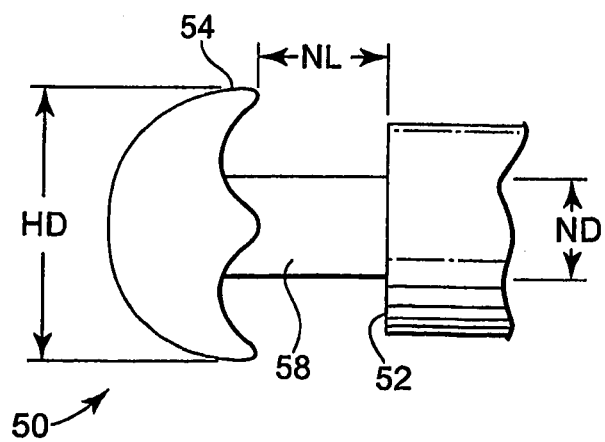
Fig. 4E

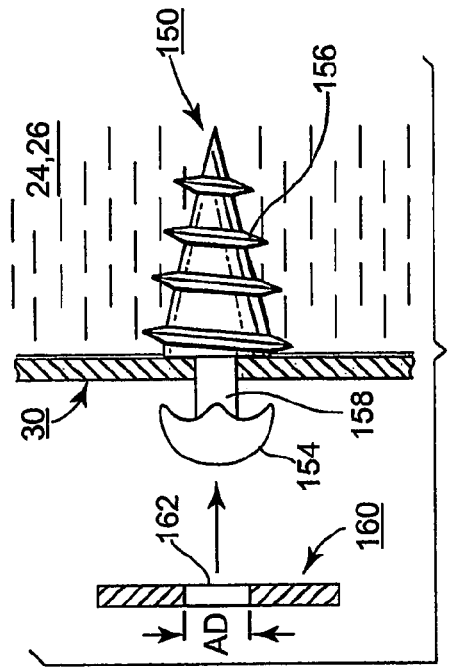
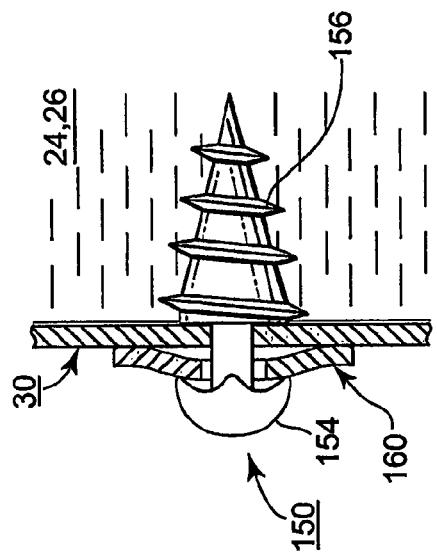
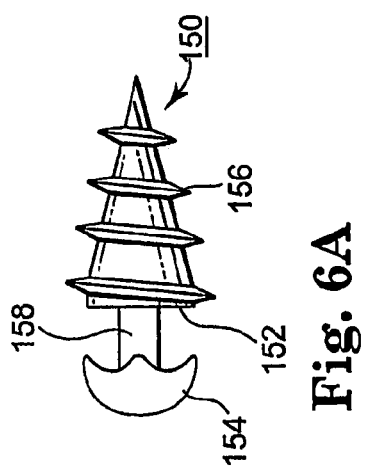

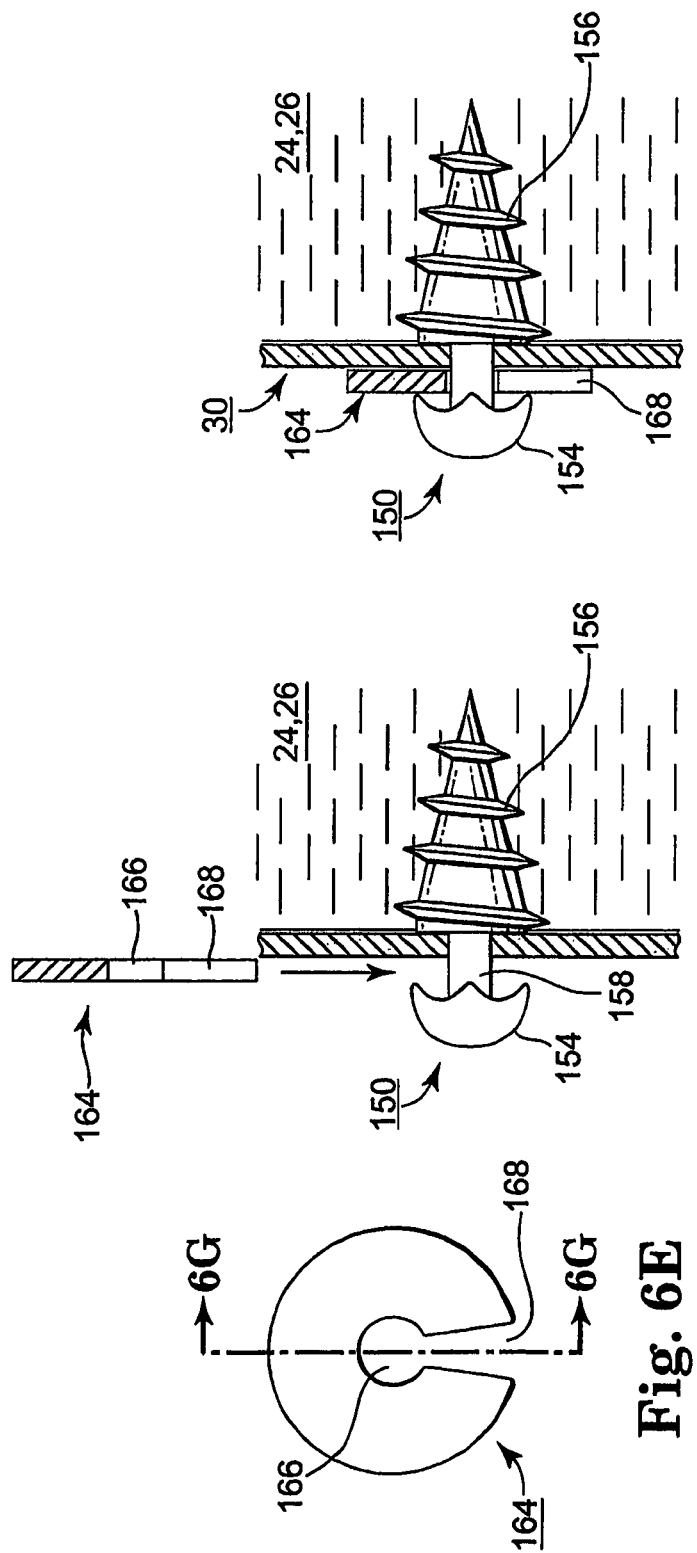

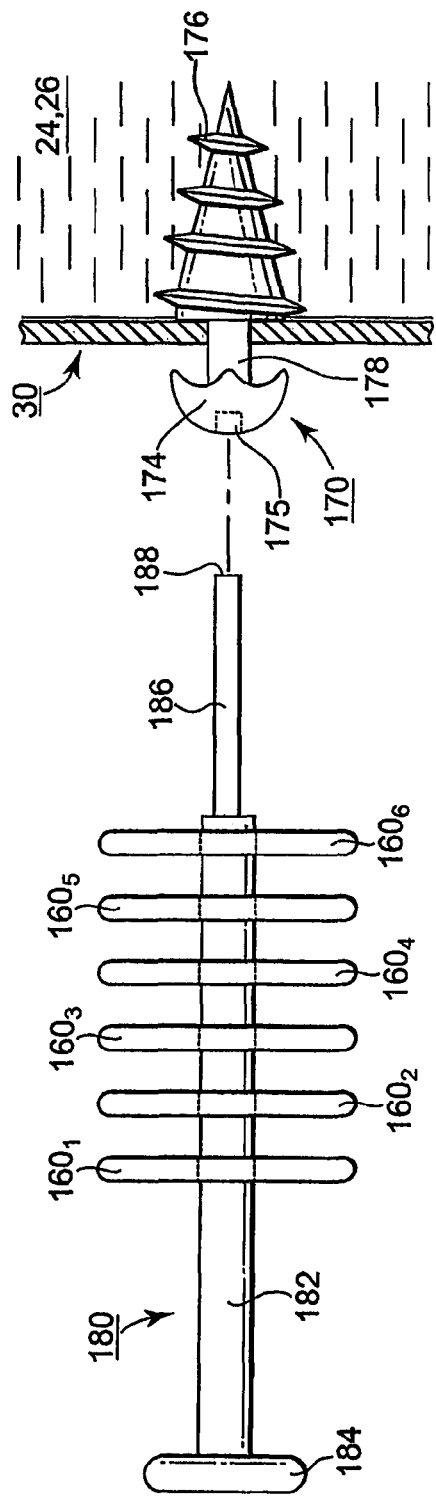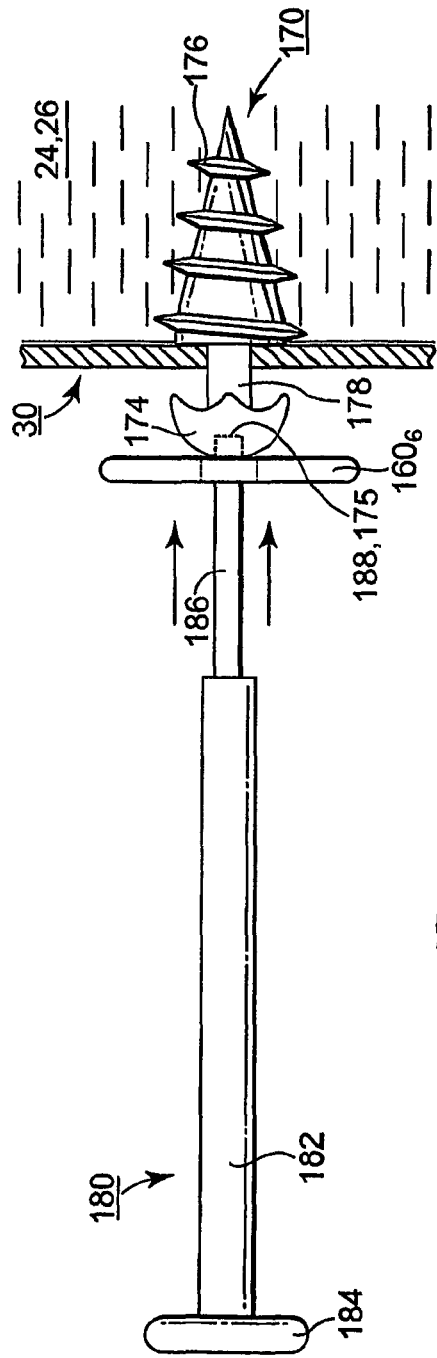
Fig. 7A
Fig. 7B

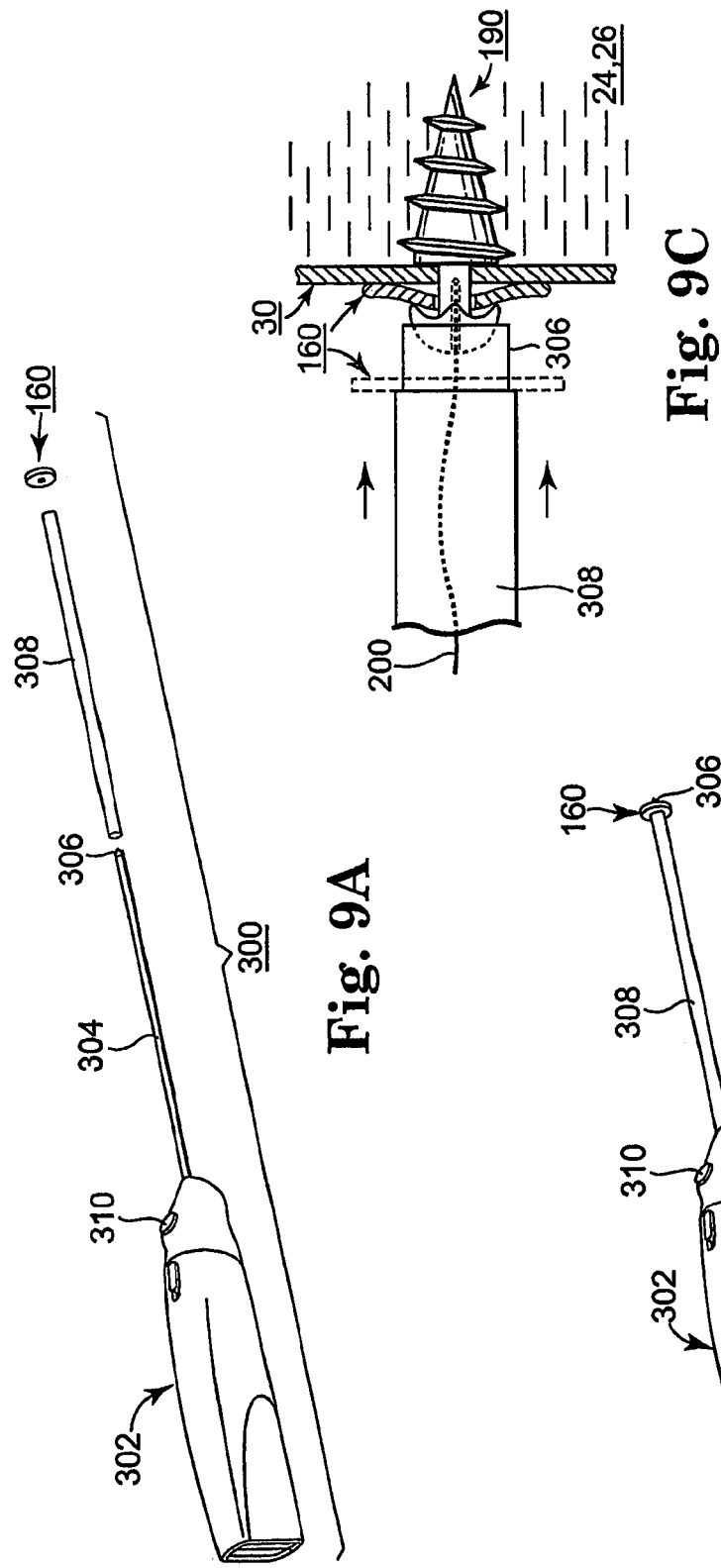

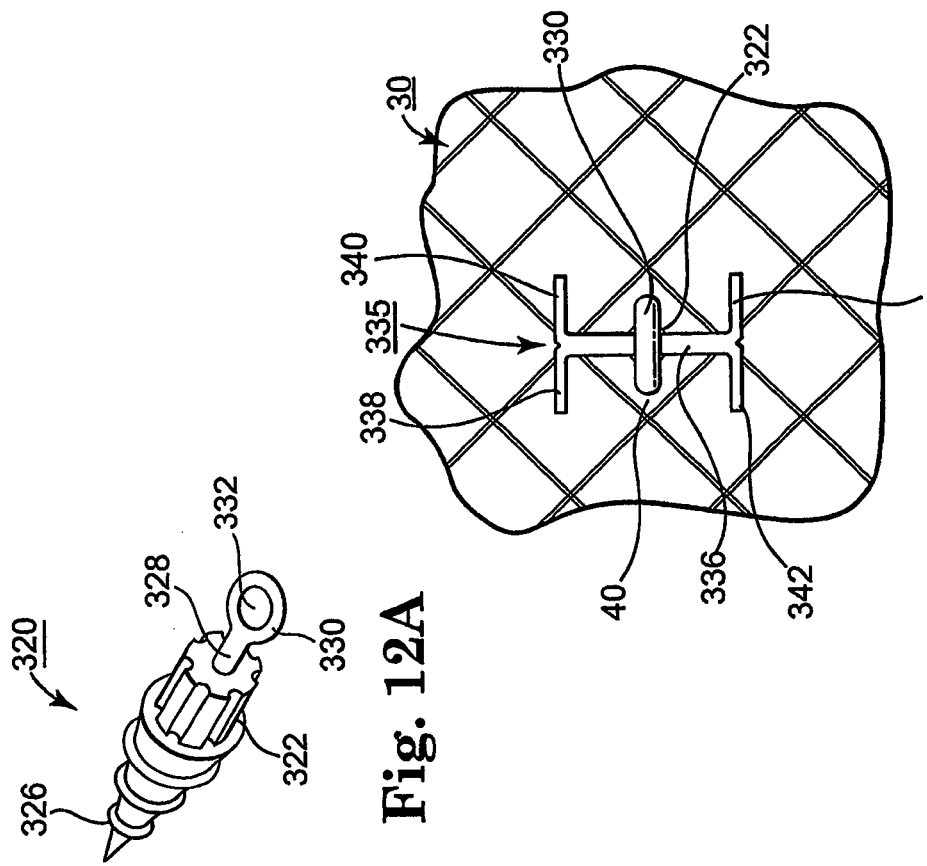
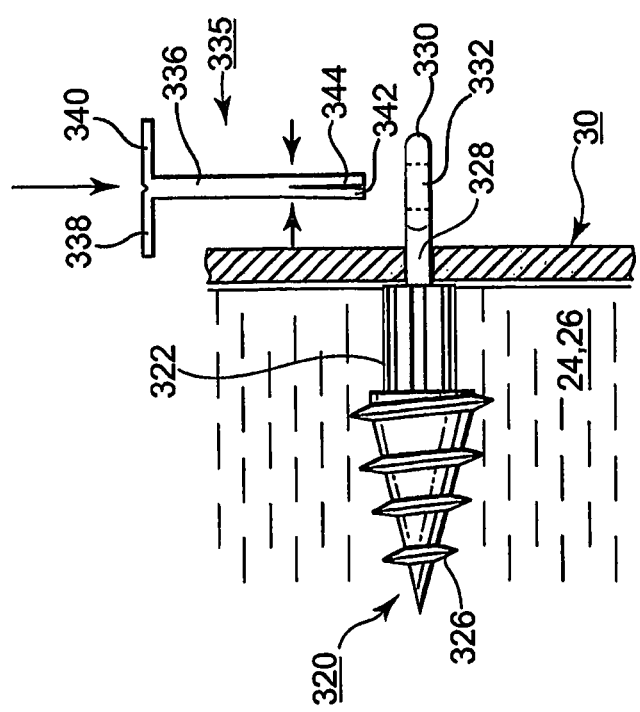

METHODS AND APPARATUS FOR SECURING A URETHRAL SLING TO A PUBIC BONE

RELATED APPLICATIONS

This application claims priority to International Application having Serial No. PCT/US2006/023872 filed Jun. 20, 2006, which claims priority to U.S. Provisional Application Ser. No. 60/692,662 filed Jun. 21, 2005, the entire contents of both are incorporated herein by reference.

The present invention pertains to surgical procedures, kits, and implants to alleviate human incontinence, and particularly to improved methods and apparatus to secure a urethral sling to pubic bone in a sub-urethral location to support the urethra and alleviate incontinence.

BACKGROUND

Incontinence is a condition characterized by involuntary loss of urine, beyond the individual's control, that results in the loss or diminution of the ability to maintain the urethral sphincter closed as the bladder fills with urine. Male or female stress urinary incontinence (SUI) occurs when the patient is physically or emotionally stressed.

One cause for this condition is damage to the urethral sphincter or loss of support of the urethral sphincter, such as can occur in males after prostatectomy or following radiation treatment, or that can occur due to pelvic accidents and aging related deterioration of muscle and connective tissue supporting the urethra. Other causes of male incontinence include bladder instability, over-flowing incontinence and fistulas.

The female's natural support system for the urethra is a hammock-like supportive layer composed of endopelvic fascia, the anterior vaginal wall, and the arcus tendineus (a distal attachment to the pubic bone). Weakening and elongation of the pubourethral ligaments and the arcus tendineus fascia pelvis, weakening of the endopelvic fascia and pubourethral prolapse of the anterior vaginal wall, and their complex interaction with intraabdominal forces are all suspected to play a role in the loss of pelvic support for the urethra and subsequent hypermobility to an unnaturally low non-anatomic position, leading to urinary incontinence.

Females can also exhibit cystocele, a condition due to laxity of the pelvic floor wherein the bladder extrudes out and downwards causing SUI. The severity of this bladder collapse is rated between Grades one through four. In Grade four cystocele, the bladder extrudes out of the vaginal opening. The treatment of choice for this condition includes the reduction or dosing of the pelvic floor opening from which the bladder descends using sutures. As noted below, other procedures involving implantation of a urethral sling are also gaining acceptance.

In general, continence is considered to be a function of urethral support and coaptation. For coaptation to successfully prevent or cure incontinence, the urethra must be supported and stabilized in its normal anatomic position.

The present application is directed to the treatment of SUI and chronic urinary incontinence due to inability of the urethral sphincter to dose or remain closed as bladder fluid pressure builds. Currently, incontinence treatments of choice involve implantation of a Kaufman Prosthesis, an artificial sphincter (such as the AMS-800 Urinary Control System available from American Medical Systems, Inc.), or a urethral sling procedure in which a urethral sling is inserted beneath the urethra and advanced in the retro pubic space. Peripheral portions of the elongated urethral sling are affixed to bone or body tissue, and a central portion of the elongated urethral sling extends under the urethral or bladder neck to provide a platform that compresses the urethral sphincter, limits urethral distention, and pelvic drop, and thereby improves coaptation.

Male and female urethral sling procedures are disclosed in commonly assigned U.S. Pat. Nos. 6,652,450 and 6,382,214, for example, and further female urethral sling procedures are described in commonly assigned U.S. Pat. No. 6,641,524, for example, and publications and patents cited therein. The implantation of certain urethral slings involves the use of delivery systems configured for and techniques that involve transvaginal, transobturator, suprapubic and pre-pubic exposures or pathways.

The above-referenced '214 patent describes apparatus and methods for treatment of male incontinence and female cystocele repair in which a urethral sling material is positioned between the descending pubic rami of the pubic bone. In such an operation a "hammock-like" urethral sling material is sutured below the urethra in males, or below the posterior bladder wall in the case of cystocele in females. The urethral sling material may comprise synthetic material or cadaveric or autologous fascia and may or may not be absorbable over time.

In the male case, the urethral sling applies passive compression against the bulbar urethra. The compression, either by itself or in conjunction with urethral mobility, prevents urine leak during strain. If additional passive pressure is required on the urethra after surgery is completed, collagen or other bulky material can be injected with a tiny needle through the perineum, causing more pressure created by the bulky material on one side (the lower or caudal side) by the urethral sling, and on the other (the upper or superior) side compressing the urethra. An example of a urethral sling sutured to and extending between four bone screws fixed to the descending pubic rami is depicted in FIG. 12 of the above-referenced '214 patent.

One minimally invasive surgical procedure that incorporates the teachings of the above-referenced '214 patent to alleviate mild to moderate male SUI is performed employing the InVance™ Male Urethral Sling System for implanting the InteMesh™ Synthetic Surgical Mesh (both available from American Medical Systems, Inc.) in a manner generally described in the above-referenced '214 patent and depicted in FIGS. 1-3. The InteMesh™ Synthetic Surgical Mesh is about 4 cm×7 cm and knitted from a supple polyester material coated with silicone, the knitted mesh having a pore size that allows for tissue ingrowth during chronic implantation. The InVance™ Male Urethral sling System includes four to six, typically, titanium bone screws and a disposable, battery powered, inserter or driver. Each bone screw has a distal self-tapping spiral thread and a length of No. 1 Prolene suture extending proximally from the bone screw.

In the implantation procedure, the patient is first placed in the lithotomy position and draped, and the surgical field is prepared. A 16 French Foley catheter, for example, is inserted into the urethra, the catheter balloon is inflated t to assist the surgeon in identifying the urethra during dissection, and the scrotum is elevated. A vertical incision is made over the midline in the perineum, and the skin and subcutaneous tissues are dissected free. The bulbocavernous muscle is then exposed, and dissection is carried out posteriorly to the area of the transverse perineum to completely free the bulbar urethra. Lateral dissection is used to expose the corpora cavernosum and the descending pubic rami.

The six titanium bone screws or anchors are then screwed, one at a time, into the inner portion of the descending pubic rami of the pubic bone using the battery-powered driver. The bone screws are screwed fully into the pubic bone so that the No. 1 Prolene sutures extend outward from each bone. The location of each bone screw and the order of bone screw insertion can be selected by the surgeon. In one approach, the first pair of bone screws is inserted just below the symphysis, the second pair is inserted just proximal to the level of the ischial tuberosity, and the third pair is inserted intermediate the first and second pair.

The InteMesh™ Synthetic Surgical Mesh is then applied against the array of bone screws bridging the lower surface of the bulbar urethra between the descending pubic rami to determine where the sutures will be passed through the mesh pores and tied off. The sutures extending from one of the descending pubic rami may be first passed though selected mesh pores and tied off employing several surgeon's suture knots. Tension is then applied to the other side or end of the urethral sling as it is drawn against the other pubic ramus to determine where the bone screw sutures should be passed through the mesh pores and tied off.

The determination of the appropriate tension may be accomplished using a cough test or Retrograde Perfusion Pressure (RPP) test. To perform a RPP test, the Foley catheter balloon is then deflated, and the Foley catheter is withdrawn and connected to a sterile saline perfusion line. A zero pressure state is obtained by lowering the bag to the level of the symphysis. The tip of the catheter is repositioned at the penoscrotal angle, and the urethral resistance to start of flow or leakage is recorded (by distance of the bag above the level of the symphysis). In patients under anesthesia suffering from sphincter incontinence, the urethral resistance is very low. Tension is then applied to the untied side of the urethral sling by advancing the end of the urethral sling along the sutures toward the bone screws so that the urethral sling bears against the bulbar urethra. The mesh urethral sling compresses the bulbar urethra as it is adjusted in tension to increase urethral resistance to withstand a pressure selected between 30 and 60 cm of water. The sutures are then tied to maintain the selected tension.

The Foley catheter is then advanced to the bladder (which should advance without difficulties), and the wound is irrigated with Bethadine solution and closed in layers. Subsequently, the Foley catheter is removed after 2 hours, and the patient can be discharged home on oral antibiotics and pain medication after completing a successful voiding trial.

The above-referenced '214 and '524 patents also disclose procedures for repairing a cystocele using retropubic and lateral pubic bone anchors. The surgery disclosed in the '214 patent is indicated for patients with grade four cystocele and urethral hypermobility. The procedure repairs the central defect, the lateral defect, approximates the cardinal ligaments to the midline, and creates a urethral sling of the urethra.

After preparation and draping, a Foley catheter is inserted in the bladder. Once the catheter is in place, a "goal post" incision is made. The vertical bars of the goal post extend laterally from the distal urethra to the horizontal bar that is made just proximal to the bladder neck. The vertical bars reach the vaginal cuff.

After creation of the goal post incision, the vaginal wall is dissected free to expose the perivesical fascia laterally and the cardinal ligaments posteriorly. A figure eight 2-0 absorbable suture is applied to approximate the cardinal ligament to the midline without tying it. If an enterocele sac is encountered, it should be repaired at this stage.

The retropubic space is then entered over the periurethral fascia at the level of the vertical bars of the incision, and the urethropelvic ligaments are exposed. Two fascial anchors (the upper pair) are inserted into the tissue of the suprapubic area. Each of these anchors comprises a bone screw having a distal self-tapping screw thread of the type described above with a No. 1 Prolene suture attached to the proximal end of the bone screw.

In an alternative embodiment, at this stage of the procedure, the retropubic space is not open and two bone anchors or screws of the type described above are applied to the inner surfaces of the symphisis using a right angle drill.

After application of the first set of anchors, a second pair of bone anchors or screws of the type described above are applied to the inner surface of the descending pubic rami of the symphysis.

Once the four bone screws are in place, the bladder prolapse is reduced using a moist sponge over a right angle retractor. Alternatively, a Dexon mesh is applied and left in place. The lower pair of Prolene sutures is then used to incorporate the perivesical fascia and the cardinal ligaments area. Interrupted 2-0 absorbable sutures are used to approximate the perivesical fascia to the midline over the Dexon mesh.

A variation on this procedure is set forth in commonly assigned, U.S. Patent Application Publication No 2002/0183762 to provide urethral support and coaptation employing the InFast™ Ultra Transvaginal Urethral sling System for implanting a urethral sling selected from among the InteXen™ Porcine Dermal Matrix or the InteDerm™ Allograft Dermal Matrix or the InteLata™ Allograft Fascia Lata (all available from American Medical Systems, Inc.). The selected urethral sling is intended to be cut to size and in a T-shape to fit between the bone screws and to be attached thereto as described above. The InFast™ Ultra Female Urethral sling System includes four, typically, titanium bone screws and a disposable, battery powered, inserter that positively engages the bone screw to drive it into bone. In this system, a length of No. 1 Prolene suture is passed through a metal ring extending proximally from the bone screw, and the ends of the suture are joined to needles adapted to be passed through the urethral sling. A distal end of a drive shaft of the battery-powered inserter engages the bone screws, and the drive shaft is shaped to enable orientation of the screw threads toward the posterior aspect of the pubic bone. Other types of bone anchors that include a penetrating tip, a shaft, and a suture threaded through the shaft and that are adapted to be inserted into bone are disclosed in commonly assigned U.S. Pat. Nos. 6,635,058 and 6,746,455.

The tensioning of the selected urethral sling is accomplished in this procedure as the suture needles are passed through the urethral sling, and the urethral sling is pressed against the bone surface. The suture needles are severed, and the suture ends are tied together. The tied suture knot is slid upward and posteriorly (behind the bone) to ensure juxtaposition of the sling end to the bone surface.

The above-described bone screws are intended to be driven into the bone until completely embedded with the suture extending out of the self-tapped bore in the bone.

Thus, in the above-described procedures, the urethral sling in maintained in place, and sling tension is adjusted and applied through the tied sutures. The procedure of initially tensioning and tying the sutures takes an undue amount of the surgical time, up to 15-25 minutes as observed in some instances employing the InVance™ Male Urethral Sling System for implanting the InteMesh™ Synthetic Surgical Mesh. Moreover, it is sometimes difficult to achieve the tension in the urethral sling that is sufficient to constrict the urethral sphincter to provide urethral resistance to leakage at the selected water bag height, e.g. at 60 cm.

If the resulting sling tension is not adequate, it may be necessary to untie the tied sutures to readjust tension including possibly repositioning the bone screw in the pubic bone or the sutures extending through the urethral sling. Tying, untying and retying the suture knots consumes further time. Thus, it would be desirable to simplify the process of and to reduce the amount of time that it takes to detach, adjust tension, and reattach the urethral mesh to the sutures extending from bone screws.

Moreover, the sutures may have been trimmed at the knot following an earlier tying. Applying tension through and retying the trimmed sutures may be difficult to accomplish. Therefore, it would be desirable to simplify the process of tensioning and retying the sutures in a manner that is not compromised by trimming the suture length.

In addition, redundant knots are often tied to increase reliability of the suture knot, and the size of the knots so formed can irritate adjacent enervated tissue, causing discomfort to the patient. Consequently, it would be desirable to minimize the physical size of suture fixation of the urethral sling to the bone anchors or screws.

Various types of bone anchors that include a penetrating tip, a shaft, and a head and are adapted to be inserted into bone are disclosed in commonly assigned U.S. Pat. Nos. 6,328,744, 6,387,041, 6,544,273, 6,730,110, and 6,843,796. In certain embodiments disclosed in the '041 patent, for example, the head extends at an angle to the shaft axis, and may comprise laterally extending arms or may comprise a circular plate, a sphere or a half-sphere. In use, the tip is advanced through the sling so that the sling bears against the shaft and is maintained there by the head.

SUMMARY

The preferred embodiments of the present invention incorporate a number of inventive features that address the above-described problems that may be combined as illustrated by the preferred embodiments or advantageously separately employed.

The kits, tools, and/or components of the preferred embodiments of the present invention may be employed to affix a sling to a bone or bones, in particular, a urethral sling to pubic bones. The urethral sling may be of any type having opposed sling sides and extending between a first sling end adapted to be coupled to a first pubic bone and a second sling end adapted to be coupled to a second pubic bone to fix the urethral sling in a sub-urethral location to support the urethra and alleviate incontinence. The urethral sling may be formed of material having sling openings extending through it at least in portions adjacent the first and second sling ends. In the case that the urethral sling is formed of a mesh having mesh pores for tissue ingrowth, mesh pores may be selected to function as sling openings. Alternatively, the urethral sling may be formed of a material capable of being perforated in the surgical procedure to form sling openings extending through it at least in portions adjacent the first and second sling ends.

The kits, tools and/or components of the preferred embodiments of the present invention include bone anchors with exposed bone anchor heads and necks configured to receive and support a urethral sling applied to the bone anchors with retainers applied against the urethral sling to retain portions of the urethral sling between the bone anchor heads and the pubic bones.

In one aspect of the present invention, the bone anchor is formed with an anchor shaft or body having an anchor body axis extending from a proximal anchor head through an anchor neck to a distal anchor tip. The parts of the anchor body have length dimensions aligned with the anchor body axis and lateral dimensions lateral to the anchor body axis. Thus, the anchor body may have a neck dimension and a head dimension lateral to the anchor body axis. The neck and head dimensions may be a diameter or cross-section area when the head and neck are substantially circular extending laterally through 360° rotation about the anchor body axis. The neck and head dimensions may be a length or thickness in a direction lateral to the anchor body axis when the head and neck are not substantially circular and do not extend laterally through 360° rotation about the anchor body axis. The terms "lateral" and "laterally" may reference dimensions or directions or vectors that are substantially transverse to the bone anchor axis or that are not transverse to the bone anchor axis.

In a further aspect of the invention, the bone anchor is reduced in a neck dimension or cross-section from a head dimension or cross-section of the proximal anchor head lateral to the bone anchor axis. The anchor head dimension is selected to fit through the sling opening as the urethral sling is pressed against the bone anchor head. The urethral sling is tensioned as it is applied in the same manner into engagement with the remaining anchor heads, and the urethral sling is thereby engaged and tensioned against the anchor necks between the pubic bones and the anchor heads. The urethral sling may be quickly manually detached and reattached to change sling tension as tension testing dictates.

In another aspect of the invention, a kit is provided comprising at least one bone anchor having an anchor head and at least one sling retainer that engages with the anchor head or anchor neck to bear against the urethral sling to inhibit detachment of the urethral sling from the bone anchor.

In certain embodiments, the retainer has a retainer body that is shaped having a laterally extending slot extending to or providing a retainer bore that is sized and shaped to engage the anchor neck. In use, the sling retainer is applied to the anchor neck inserted in bone by laterally advancing the retainer body with the anchor neck positioned in the slot toward the bone anchor axis until the anchor neck is seated in the anchor bore.

In other embodiments, the anchor body is resilient and has a retainer bore extending through it having a bore cross-section area less than the anchor head cross-section area. Each anchor head is extended through the sling mesh or a hole prepared in a sling fabric or tissue. Sling tension testing may proceed and repositioning may occur. The resilient annular sling retainer is fitted against the urethral sling by expansion of the retainer bore to snap the sling retainer over the proximal anchor head and entrap it within the anchor neck.

In yet another aspect of the present invention, a suture is attached to and extends proximally from the proximal anchor head. The suture extending proximally from the proximal anchor head is adapted to be threaded through a sling opening before the anchor head is extended through the sling opening. Sling tension testing may proceed and repositioning may occur until satisfactory sling tension is achieved. The suture functions as a retainer guide so that a resilient, annular sling retainer may be moved distally over the suture and fitted, by expansion of the retainer bore, to snap over the proximal anchor head and against the urethral sling entrapped by the anchor neck. The suture may be tied off and trimmed after adequate tension is achieved and with fewer knots to reduce suturing time and the final exposed suture bulk.

In preferred embodiments of this aspect of the invention, sling retainer dispensing tools are provided that facilitate application of the sling retainers over the sutures and/or anchor heads and/or against the anchor necks to press and entrap the urethral sling material against the bone.

Further embodiments of bone anchors employ anchor heads configured to accept particular sling retainers to bear against the urethral sling to retain it in place.

Advantageously, procedures for attaching the urethral sling to bone anchors or anchors are simplified to shorten the surgical time, the tensioning and fixation are made more reliable, and the resulting suture knots are reduced in size or eliminated.

Bone anchors usable in the practice of the present invention may comprise bone screws having spiral thread bone fixation mechanisms adapted to be screwed into bone or tapered, pointed, bone tack bone fixation mechanisms adapted to be advanced into bone, as disclosed for example in the above-referenced, commonly assigned '058, '273 and '041 patents, or any other form of bone fixation mechanism.

These and other advantages and features of the present invention will be more readily understood from the following detailed description of the preferred embodiments thereof, when considered in conjunction with the drawings, in which like reference numerals indicate identical structures throughout the several views, and wherein:

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

FIG. 4A is an end view of one embodiment of a bone screw adapted to engage and retain the mesh of the urethral sling of FIGS. 2 and 3 without sutures;

FIG. 4B is a side view of the bone screw of FIG. 4A;

FIG. 4C is a plan view in partial section of the bone screw of FIGS. 4A and 4B engaging and retaining the mesh of the urethral sling of FIGS. 2 and 3 to pubic bone;

FIG. 4D is a plan view in partial section of the bone screw of FIGS. 4A and 4B engaging and retaining the mesh of the urethral sling of FIGS. 2 and 3 to pubic bone and under tension;

FIG. 4E is an enlarged partial side view of the mesh engaging head and neck of the bone screw of FIG. 4A;

FIG. 6A is a side view of a further embodiment of a bone screw adapted to engage and retain the mesh of the urethral sling of FIGS. 2 and 3 without sutures;

FIG. 6B is a top view of a first embodiment of a sling retainer employed with the bone screw of FIG. 6A to enhance surface area contact with and retention of the mesh of the urethral sling of FIGS. 2 and 3 (for example);

FIG. 6C is a plan view in partial section of the bone screw of FIG. 6A engaging the mesh of the urethral sling of FIGS. 2 and 3 and the sling retainer of FIG. 6B positioned to be fitted over the bone screw head to bear against the mesh of the urethral sling of FIGS. 2 and 3 to enhance retention of the mesh to the pubic bone;

FIG. 6D is a plan view in partial section of the bone screw of FIG. 6A engaging the mesh of the urethral sling of FIGS. 2 and 3 and the sling retainer of FIG. 6B fitted over the bone screw head to bear against the mesh of the urethral sling of FIGS. 2 and 3 to enhance retention of the mesh to the pubic bone;

FIG. 6E is a top view of a second embodiment of a sling retainer employed with the bone screw of FIG. 6A to enhance surface area contact with and retention of the mesh of the urethral sling;

FIG. 6F is a plan view in partial section of the bone screw of FIG. 6A engaging the mesh of the urethral sling of FIGS. 2 and 3 and the sling retainer of FIG. 6E positioned to be fitted over the bone screw head to bear against the mesh of the urethral sling of FIGS. 2 and 3 to enhance retention of the mesh to the pubic bone;

FIG. 6G is a plan view in partial section of the bone screw of FIG. 6A engaging the mesh of the urethral sling of FIGS. 2 and 3 and the sling retainer of FIG. 6E fitted over the bone screw head to bear against the mesh of the urethral sling of FIGS. 2 and 3 to enhance retention of the mesh to the pubic bone;

FIG. 7A is a plan view in partial section of the bone screw of FIG. 6A engaging and retaining the mesh of the urethral sling of FIGS. 2 and 3 to pubic bone and a sling retainer dispensing tool poised to fit a sling retainer of FIG. 6C or 6F over the bone screw head to bear against the mesh of the urethral sling of FIGS. 2 and 3 to enhance retention of the mesh to the pubic bone;

FIG. 7B is a plan view in partial section of the bone screw of FIG. 6A engaging and retaining the mesh of the urethral sling of FIGS. 2 and 3 to pubic bone and a sling retainer dispensing tool positioned to fit a sling retainer of FIG. 6C or 6F over the bone screw head to bear against the mesh of the urethral sling of FIGS. 2 and 3 to enhance retention of the mesh to the pubic bone;

FIG. 9A is a perspective exploded view of a powered screwdriver having a screwdriver tip for engaging and rotating the head of a bone screw of FIG. 8A or FIG. 6B and adapted to support a sling retainer to be applied over the bone screw head to bear against mesh of the urethral sling of FIGS. 2 and 3 to enhance retention of the mesh to pubic bone;

FIG. 9B is a perspective view of the powered screwdriver of FIG. 9A supporting a sling retainer in position proximate the screwdriver tip FIG. 9C is a plan view in partial cross-section of the disposable tool of FIGS. 9A and 9B supporting a sling retainer and positioned over the suture of the bone screw of FIG. 8A to couple the screwdriver tip to the bone screw head and apply the sling retainer over the bone screw head to bear against the mesh of the urethral sling of FIGS. 2 and 3 to enhance retention of the mesh to the pubic bone;

FIG. 12A is a perspective view of a further embodiment of a bone screw formed with a bone screw head adapted to pass through a mesh pore of the urethral sling of FIGS. 2 and 3;

FIG. 12B is a plan view in partial section of the bone screw of FIG. 12A engaging and retaining the mesh of the urethral sling of FIGS. 2 and 3 to pubic bone through the use of a flexible H-shaped sling retainer fixed to the bone screw head;

FIG. 12C is an end view of the bone screw of FIG. 12A engaging and retaining the mesh of the urethral sling of FIGS. 2 and 3 to pubic bone through the use of the flexible H-shaped sling retainer inserted through a transverse bore of the bone screw head;

Figure 1:
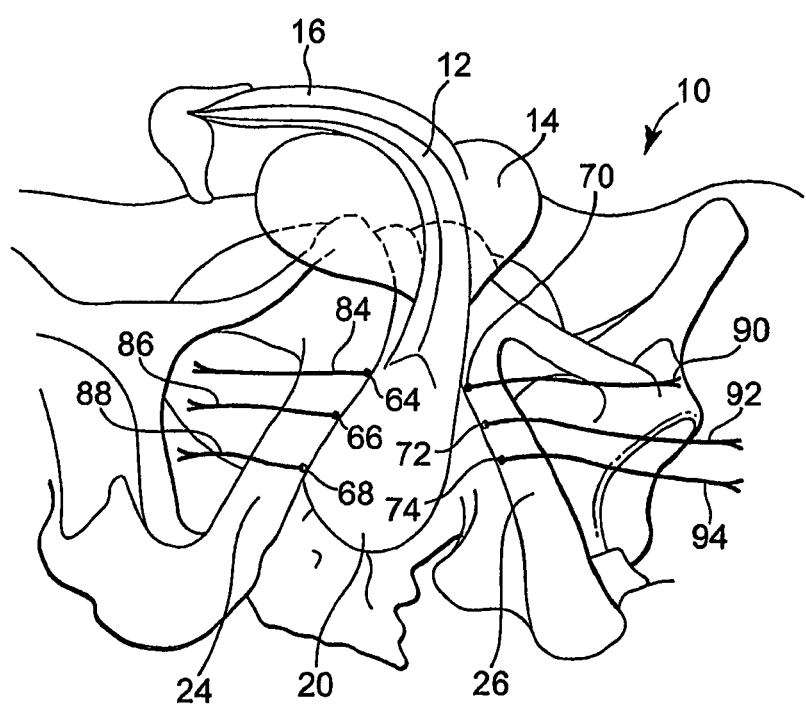
FIG. 1 is a schematic illustration of the fixation of bone anchors, e.g., bone screws, to descending pubic rami with sutures extending from the bone screws in accordance with the prior art.

It will be understood that the drawing figures are not necessarily to scale.

DETAILED DESCRIPTION

In the following detailed description, references are made to illustrative embodiments of methods and apparatus for carrying out the invention. It is understood that other embodiments can be utilized without departing from the scope of the invention. Preferred methods and apparatus are described for affixing urethral slings to pubic bones, particularly the descending pubic rami.

It will be understood that the term "urethral sling" encompasses any type of sling, tape, hammock or the like that supports and or/applies compression to the urethra. One exemplary form of urethral sling is illustrated in the figures and described below in use of the kits, tools, and/or components of the preferred embodiments of the present invention that is formed of a mesh having mesh pores that facilitate tissue ingrowth. As noted above, the urethral sling may be formed of any biocompatible flexible sheet material known in the art with or without pores or sling openings through the sheet material.

Furthermore, while the bone anchor embodiments are illustrated and described having an anchor body bearing a bone fixation mechanism comprising a spiral thread adapted to be screwed into bone, it will be understood that the principles of the present invention are applicable to other forms of bone anchors.

Figure 2:
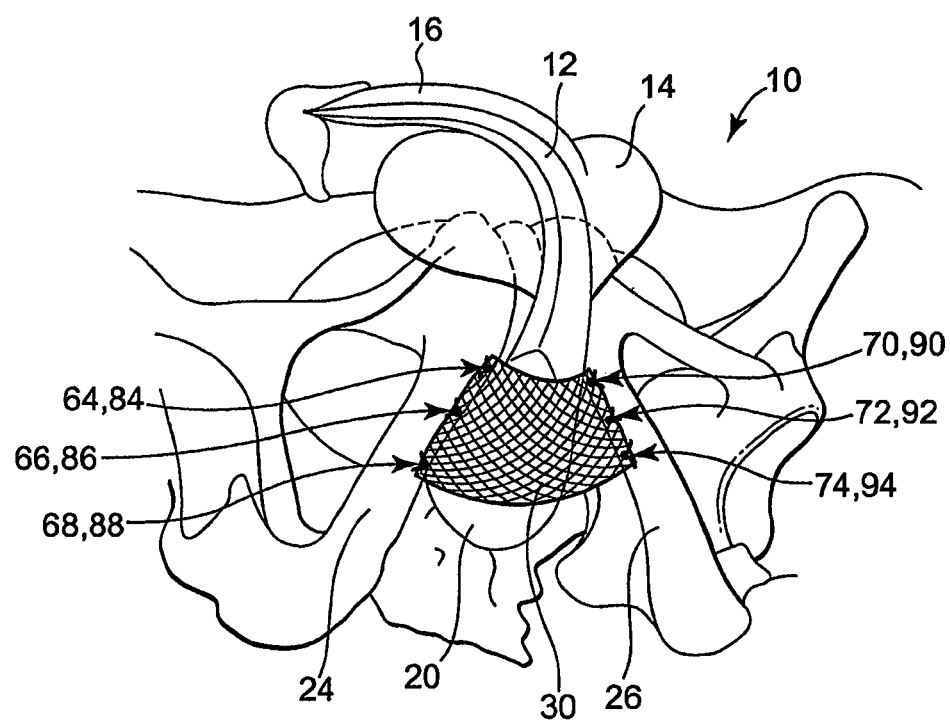
FIG. 2 is a schematic illustration of the fixation of a urethral sling to the bone screws with the sutures extending from the bone screws in accordance with the prior art.

Referring to FIGS. 1 and 2, the male anatomy in the pelvic region 10 is depicted schematically to illustrate how a urethral sling 30 is affixed to the right and left descending pubic rami 24 and 26 to extend across and support the male urethra 12 in the manner described above, for example, in the procedure employing the InVance™ Male Urethral Sling System for implanting the InteMesh™ Synthetic Surgical Mesh urethral sling.

Figure 3:
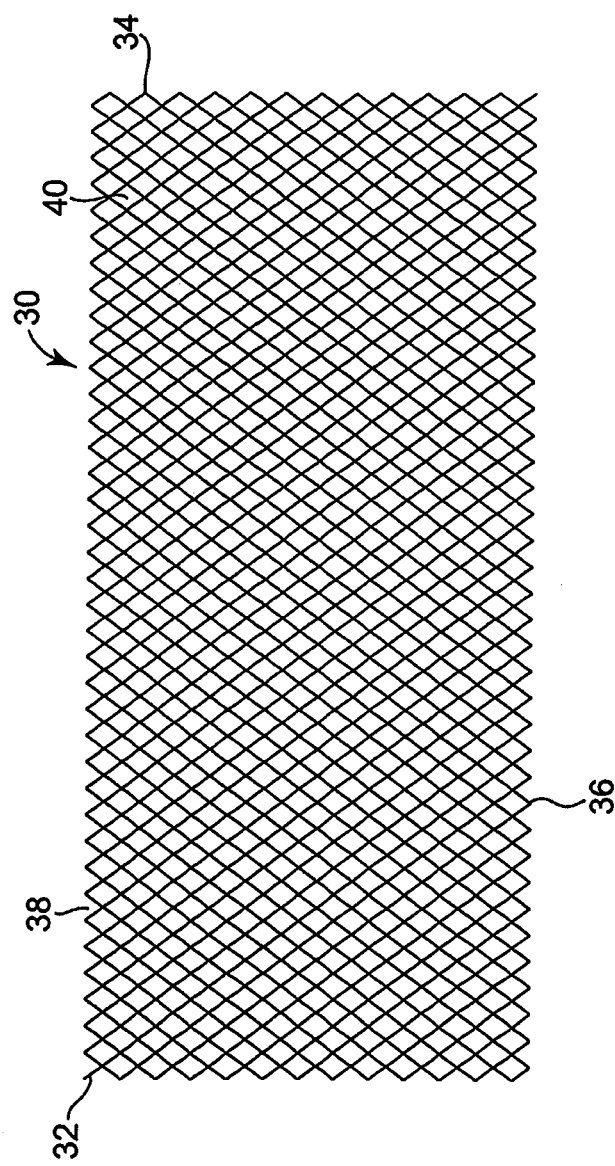
FIG. 3 is an enlarged plan view of a prior art urethral sling formed of a mesh and adapted to be attached to the descending pubic rami as shown in FIG. 2.

An embodiment of the urethral sling 30, which can correspond to the InteMesh™ Synthetic Surgical Mesh urethral sling, is depicted in greater detail in FIG. 3. In a preferred embodiment, the urethral sling 30 is knitted into a mesh from a supple polyester yarn to have a plurality of sling openings comprising mesh pores 40 bounded by yarn strands and may be coated with medical grade silicone rubber. The knitted mesh pores 40 have a pore size that allows for tissue ingrowth therethrough during chronic implantation. The urethral sling 30 extends end-to-end between first and second sling ends 32 and 34 and side-to-side between first and second sling sides 36 and 38.

Returning to FIGS. 1 and 2, as noted above, the surgical field is prepared after the patient, placed in the dorsal lithotomy position and draped. The scrotum 14 and penis 16 are elevated, a vertical incision is made over the midline in the perineum of the skin and subcutaneous tissues (not shown) are dissected to the side to expose the bulbocavernous muscle 20. Lateral dissection is used to expose the corpora cavernosum 22 and the surfaces of the descending pubic rami 24 and 26.

As shown in FIG. 1, the illustrated fixation of the surgical urethral sling 30 is effected employing six titanium bone screws 64, 66, 68, 70, 72, 74 sequentially driven by a disposable, battery powered, inserter or driver (not shown). Each bone screw 64, 66, 68, 70, 72, 74 has a distal self-tapping spiral thread adapted to be screwed into bone when the screw tip is applied to the bone surface and the driver is powered. A pair of No. 1 Prolene sutures 84, 86, 88, 90, 92, 94 extend proximally from each bone screw 64, 66, 68, 70, 72, 74, respectively. One such bone screw 64 with the pair of bone screw sutures 84 extending from the screw head is depicted in the expanded view of FIG. 5. Typically, the pair of bone screw sutures is crimped at one end into a bore of the bone screw and extends about 30 cm to bone screw suture free ends. The bone screw suture free ends can be joined as by use of ultrasonic welding to ease in handling and use of a bone screw fixation tool. The surgeon may choose to pass the joined suture free ends through a selected mesh pore, tie a knot or knots, and then trim the sutures. Or, the surgeon may first trim the sutures, separately pass the severed suture free ends through a common or separate mesh pores, tie a knot or series of knots, and again trim the suture free ends.

The bone screws 64, 66, 68, 70, 72, 74 are screwed fully into the bone so that the No. 1 Prolene sutures 84, 86, 88, 90, 92, 94, respectively, extend outward of the descending pubic rami 24 and 26 as shown in FIG. 1. The surgeon can select the location of each bone screw 64, 66, 68, 70, 72, 74 and the order of insertion. In one approach depicted in FIG. 1, a first pair of bone screws 64, 70 is inserted just below the symphysis, the second pair 66, 72 is inserted proximal to the level of the ischial tuberosity, and the third pair 68, 76 is inserted intermediate the first and second pair.

The urethral sling 30 is then applied against the array of bone screws 64, 66, 68, 70, 72, 74 bridging the lower surface of the bulbar urethra 20 between the descending pubic rami 24 and 26 to determine where each suture of the respective suture pairs 84, 86, 88, 90, 92, 94 will be passed through mesh pores.

The free ends of each suture of each suture pair 84, 86, 88, 90, 92, 94 are sequentially grasped, passed through separate mesh pores and drawn tight and tied together against the mesh of the urethral sling 30.

The sutures of the suture pairs 84, 86, 88 extending from the descending pubic ramus 24 may be first passed though selected mesh pores adjacent the first sling end 32. The first sling free end 32 is then pressed against the descending pubic ramus 24. The free ends of each suture of each suture pair 84, 86, 88 are sequentially grasped, drawn tight and tied together at least two times forming several surgeon's suture knots against the mesh of the urethral sling 30 firmly holding the sling first end against the descending pubic ramus 24.

Tension is then applied to the second sling end 34 of the urethral sling 30 as it is drawn against the second pubic ramus 26 to determine where the sutures of the bone screw suture pairs 90, 92, 94 should be passed through mesh pores and tied off in the manner described above. Testing for urethral resistance to leakage may be conducted employing the techniques and instruments described above as the sutures of bone suture pairs 90, 92, 94 are drawn tight against the fabric of urethral sling 30 and tied off. The sutures of bone suture pairs 90, 92, 94 may be retracted from the initially selected pores 40 and reinserted in other pores 40 in the process of optimizing the tension. In this way, the urethral sling 30 is eventually sutured to all of the bone anchors or screws 64, 66, 68, 70, 72, 74 inserted into the descending pubic rami 24 and 26 to extend laterally across and support the bulbar urethra 20. An intermediate portion of the urethral sling 30 extends between the bone screws 64, 66, 68 and the bone screws 70, 72, and 74.

The knots made with the suture pairs 84, 86, 88, 90, 92, and 94 are relatively bulky and can cause irritation of tissues. In accordance with the present invention, the procedure for securing the urethral sling 30 to the descending pubic rami and tensioning the urethral sling 30 is simplified, the fastening elements are less bulky than the prevailing use of suture knots, and suture knots are eliminated in some embodiments.

The present invention may be practiced employing a variety of bone anchors having an anchor body comprising an anchor shaft or body having an axis and extending from a bone penetrating tip through a bone fixation mechanism to an anchor head. The anchor shaft is joined to the anchor head by an anchor neck having a neck dimension lateral to the shaft axis less than an anchor head dimension extending lateral to the shaft axis. The illustrated form of bone anchor is a self-tapping bone screw having a spiral thread bone fixation mechanism that can be manually screwed into bone with a screwdriver or screwed into bone with a motor driven, battery powered screwdriver of the type described above. In each embodiment, the bone screw head or body is configured to mate with a screwdriver tip to be rotated and screwed into a pubic bone, typically the descending pubic ramus.

The urethral sling is adapted to be applied against the anchor head to insert the anchor head through the sling opening and apply the sling against the anchor neck. For convenience, the following embodiments are described in the context of attaching the urethral sling 30 of the type depicted in FIGS. 2 and 3 formed of a mesh with sling openings comprising mesh pores 40 as described above to the descending pubic rami 24, 26 generally in at least certain of the locations of the bone screws 64, 66, 68, 70, 72, 74 or in additional locations. However, the described embodiments and techniques and their equivalents may be employed to advantageously attach any suitable urethral sling not having mesh pores but having other pre-formed sling openings extending through it or that can be perforated to make sling openings during surgery to the descending pubic rami 24, 26 or other pubic bone.

In one embodiment of the present invention depicted in FIGS. 4A-4E, a bone screw 50 is screwed into the bone of the right and left descending pubic rami 24 and 26, in substitution for each of the combined bone screw and suture pair depicted in FIGS. 1 and 2 and described above. For example, six bone screws 50 are screwed into the bone of the right and left descending pubic rami 24 and 26 where bone screws 64, 66, 68, 70, 72, and 74 are depicted in FIGS. 1 and 2. The urethral sling 30 is then attached directly to each bone screw 50.

In the depicted embodiment, the bone screw 50 is formed with a generally conical shaft or screw body 52 having a longitudinal shaft axis and extending between a proximal screw head 54 to a distal screw tip, and a spiral thread 56 extends along the generally conical screw body 52 to a distal screw tip. The screw head 54 has an external driver configuration to mate with a manual or powered screwdriver (not shown) that is employed to rotate and screw the bone screw 50 into bone. For example, the external driver configuration may be fluted or scalloped to have indentations or splines or have flats similar to a hex head that engage with female screw driving head shaped in a hexagonal shape or a Torx shape or the like. It will also be understood that the screw body 52 and the spiral screw thread 56 may take any known form employed in bone screws adapted to be screwed into bone.

In preferred embodiments, the bone screw 50 is formed having a screw neck 58 having a screw neck length NL intermediate the screw head 54 and the screw body 52. Preferably, the proximal screw head 54 is shaped to fit through a mesh pore 40 to engage the urethral sling 30 against the screw neck 58 to hold it in place extending between the right and left descending pubic rami 24 and 26. The screw neck 58 and the screw head 54 are dimensioned laterally to the longitudinal axis of the screw shaft or body 52 to enable passage of the sling over the screw head 54, by pressing the sling against the sling to force the screw head 54 through a mesh pore that is stretched in the process. For example, the screw neck 58 has a neck diameter ND less than the head diameter HD of the proximal screw head 54 and the diameter of the proximal end of the screw body 52 where it joins the screw neck 58. The diameters of the proximal end of the screw body 52 and the maximum diameter of the screw head 54 are selected to exceed the dimensions of the mesh pore 40 and may or may not be the same. The distal surface of the bone screw head 54 may be shaped to catch on the strands forming the mesh of the urethral sling 30.

In use, a plurality, e.g., six, of the bone screws 50 are screwed into the descending pubic rami 24 and 36, and the urethral sling 30 is applied against the screw head 54 of each bone screw 50 in a selected order. Each screw head 54 extends or pops through a selected mesh pore 40 as the urethral sling 30 is pressed against the screw head 54. The somewhat elastic strands of the mesh of the urethral sling 30 allow the size of the mesh pore 40 to be expanded as the screw head passes through the selected mesh pore 40. The size of the mesh pore 40 is restored when the strands are disposed between the screw head 54 and the screw body 52. The elastic strands bounding the selected mesh pore 40 bear against the reduced diameter screw neck 58. The urethral sling 30 is tensioned as it is applied in the same manner into engagement with each remaining screw head 54. The urethral sling 30 is thereby entrapped, engaged, and tensioned between each screw neck 58 of each bone screw 50 screwed into the descending pubic rami 24, 26 or other pubic bones. The urethral sling 30 may be readily detached and reattached to change sling tension as tension testing dictates.

The bone screws 50 may be screwed into the descending pubic rami 24, 26 such that the bone screw axes are perpendicular to the plane of the urethral sling 30 extending between the descending pubic rami 24 and 26 as shown in FIG. 4C. Alternatively, some or all of the bone screws 50 may be screwed into the descending pubic rami 24, 26 such that the bone screw axes are not perpendicular to the plane of the urethral sling 30 extending between the descending pubic rami 24 and 26 as shown in FIG. 4C.

Figure 5A:
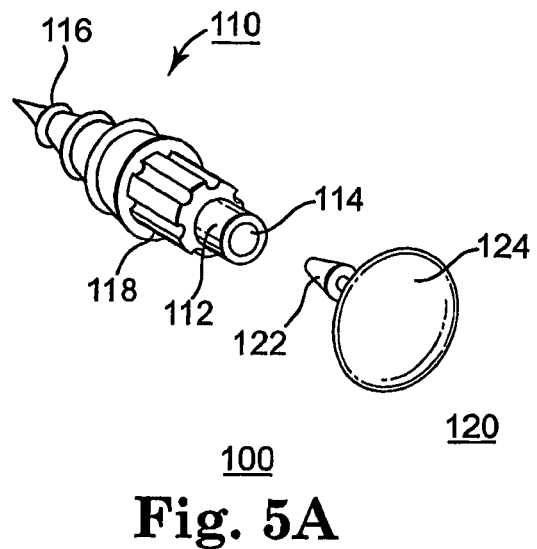
FIG. 5A is a perspective view of the components of a further embodiment of a bone screw adapted to engage and retain the mesh of the urethral sling of FIGS. 2 and 3 without sutures.
Figure 5B:
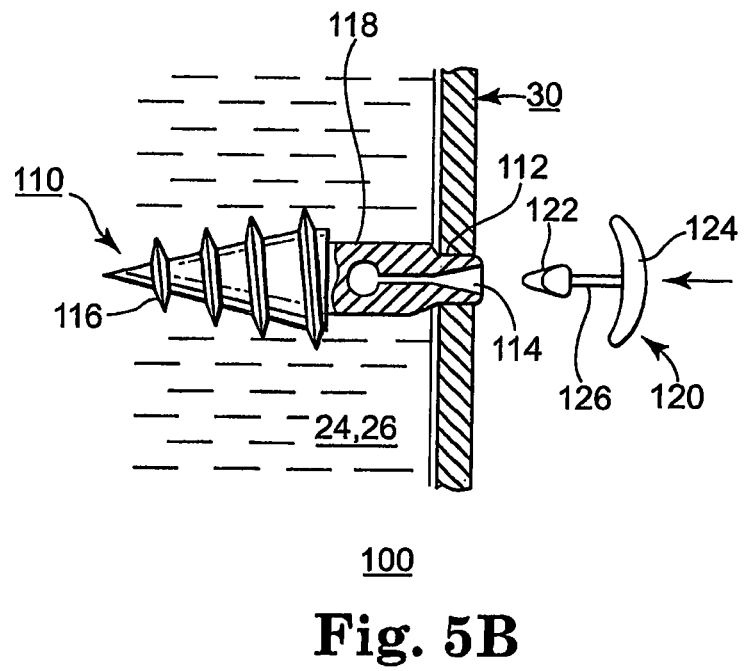
FIG. 5B is a plan view in partial section of the bone screw of FIG. 5A engaging and retaining the mesh of the urethral sling of FIGS. 2 and 3 to pubic bone.

In the embodiment of bone screw 50 depicted in FIGS. 4A-4E, the bone screw head 54 is integral with the bone screw 50. It will be understood that the bone screw head may be separate from and attachable to the bone screw body or neck. One embodiment of such a bone screw 100 comprising a bone screw shaft or body 110 and a separate screw head 120 is depicted in FIGS. 5A and 5B.

The bone screw body 110 is generally conical and extends from a proximal bone screw neck 112 through an external driver configuration or element 118 and a spiral screw thread 116 to a distal bone penetrating tip. The distal screw tip and the spiral screw thread 116 may take any known form employed in bone screws.

The external driver element 118 on a proximal portion or shoulder of the screw body 110 is shaped to mate with the screwdriver tip of a manual or powered screwdriver (not shown) that is employed to rotate and screw the bone screw body 110 into the bone. For example, the external driver configuration may be fluted or scalloped to have indentations or splines or flats similar to a hex wrench. A female screwdriver tip shaped in a complementary hexagonal shape or a Torx shape or the like can be applied over the bone screw head 110 to engage the external driver configuration.

The proximal bone screw neck 112 incorporates a proximal socket 114 that extends axially from the proximal end of the screw body 110 within the bone screw neck 112 and the external driver element 118. The socket 114 may be threaded or shaped with one or more catch.

The separate screw head 120 is formed in a tack-like shape, for example, comprising a proximal tack head 124, a distal prong 122 (for example), and a shaft 126 extending between the proximal tack head 124 and the distal prong 122. The distal prong 122 and shaft 126 are shaped and dimensioned to fit into the proximal socket 114. The distal prong 122 may engage a catch within the proximal socket 114 to resist withdrawal of the shaft 126 from the proximal socket 114. Alternatively, the shaft 126 may be threaded along its length to be screwed into mating threads formed in the proximal socket 114 to resist withdrawal of the shaft 126 from the proximal socket 114. The diameter of tack head 124 is selected to exceed and the diameter of the screw neck 112 and is selected to match or be smaller than the size of the mesh pore 40 of the urethral sling 30.

In use, a plurality, e.g., six, of the bone screw bodies 110 are screwed into the descending pubic rami 24 and 36 so that the proximal sockets 114 are accessible. A screw head 120 and the urethral sling 30 are grasped so that the distal retainer prong 122 and shaft 126 can be inserted through a selected mesh pore 40 of the urethral sling 30 and then inserted into a proximal socket 114. The steps are repeated with each screw head 120 until all screw heads 120 are affixed to bone screw bodies 110 to form bone screws 100. For example, the urethral mesh 30 may be first affixed along an end thereof to bone screws 100 screwed into one of the descending pubic rami 24, 26 and then the other end of the urethral mesh 30 may be affixed along the other end thereof to bone screws 100 screwed into the other of the descending pubic rami 24, 26. In the process, tension may be applied to the urethral mesh 30 to stretch it between the bone screws 100.

The elastic strands bounding the selected mesh pore 40 bear against the reduced diameter, screw neck 112. The urethral sling 30 is thereby entrapped, engaged, and tensioned between each screw body 110 of each bone screw 100 screwed into the descending pubic rami 24, 26 or other pubic bones. The urethral sling 30 may be readily detached and reattached to change sling tension as tension testing dictates.

In accordance with a further aspect of the invention, at least one sling retainer is provided in a kit with each bone anchor, the sling retainer having a retainer dimension exceeding a head dimension of an integral or separate anchor head and a neck engaging retainer bore. The sling retainer is adapted to be interposed between the sling and the anchor head to retain the sling against the anchor neck and to inhibit passage of the sling over the anchor head. One such sling retainer for use with a bone screw shaped generally in the manner of the bone screw 50 of FIGS. 4A-4E or the bone screw 100 of FIGS. 5A-5B to enhance the retention characteristics is depicted in FIGS. 6A-6D. The bone screw 150 of FIGS. 6A-6D is generally configured like the bone screw 50 of FIGS. 4A-4E having a generally conical shaft or screw body 152 extending between a proximal screw head 154 to a distal screw tip, and a spiral screw thread 156 extends along the generally conical screw body 152 to a distal screw tip. The screw head 154 has an external driver configuration similar to that of screw head 54 to mate with a manual or powered screwdriver (not shown) that is employed to rotate and screw the bone screw 150 into bone. The bone screw 150 is modified to have a somewhat elongated NL of screw neck 158 than screw neck 58 of bone screw 50 to accommodate the thickness of a separate retainer 150 depicted in FIGS. 6B-6D or retainer 164 depicted in FIGS. 6E-6G or other retainers described herein.

Substantially the same steps are followed to screw each bone screw 150 into the right and left descending pubic rami 24 and 26 and to fit the urethral sling 30 to each bone screw neck 158 as are described above for screwing each bone screw 50 or 100 into the right and left descending pubic rami 24 and 26 and fitting the urethral sling 30 thereto. The tension of the urethral sling 30 may be tested, and the urethral sling 30 may be detached and reattached until acceptable tension is achieved. One of the sling retainer 160 or 164 is then fitted about the screw neck 158 and against the urethral sling 30 to enhance retention during chronic implantation.

The sling retainer 160 is preferably annular in shape, like a washer, having a central retainer port or bore 162. The retainer dimension or diameter of the retainer 160 exceeds the head diameter HD (FIG. 4E) of the screw head 154. The bore diameter of the retainer bore 162 is selected to be smaller than the head diameter HD and substantially equal or exceed the neck diameter ND. The retainer 160 is formed of an elastic, bio-compatible material that can be stretched sufficiently to expand the diameter of the retainer bore 162 to the head diameter HD so that the retainer 160 can be fitted over the screw head 154 as shown in FIG. 6C. The retainer 160 is thereby entrapped between the screw head 154 and the urethral sling 30 as shown in FIG. 6D. The retainer diameter of the retainer 160 and surface area of contact of the retainer 160 to the mesh strands of the urethral sling 30 enhances retention of the urethral sling 30.

The sling retainer 164 is also preferably annular in shape, like a washer, having a central aperture 166, but further having a slot 168 extending from the retainer circumference to the central aperture 166. The outer diameter of the retainer 164 also exceeds the head diameter HD (FIG. 4E) of the screw head 154. The diameter of the central aperture 166 is selected to be smaller than the head diameter HD and substantially equal or exceed the neck diameter ND. The slot end joining the central aperture 166 is narrower than the neck diameter ND. The retainer 164 is formed of an elastic, bio-compatible material that can also be stretched sufficiently to expand the slot 168 at the central aperture 166 to the neck diameter ND so that the retainer 164 can be fitted over the neck 158 as shown in FIG. 6F. The retainer 160 is thereby entrapped between the screw head 154 and the urethral sling 30 as shown in FIG. 6G. The diameter of the retainer 160 and surface area of contact of the retainer 160 to the mesh strands of the urethral sling 30 enhances retention of the urethral sling 30.

In a still further aspect of the present invention, a kit may be provided including sets of the resilient annular retainers 160 and/or 164 that the surgeon may selectively employ as described above. It will be appreciated that the fixation of the resilient annular retainer 160 over the screw head 154 or a slotted annular retainer 164 over the screw neck 158 may be facilitated through the use of a dispenser rather than attempting to simply manually placing and pressing the retainer 160 or 164 onto the screw neck 158. In one embodiment, the dispenser stores the required number of retainers 160 or 164, aligns a retainer 160 or 164 with the bone screw 150, and facilitates transfer of the retainer 160 or 164 from the dispenser onto the screw neck 158.

One such exemplary retainer dispenser 180 is depicted in FIGS. 7A and 7B for use in dispensing an annular retainer 160 onto the screw neck 178 of a further bone screw 170. The retainer dispenser 180 comprises an elongated dispenser shaft 182 extending between a proximal dispenser shaft end 184 and a distal dispenser shaft end 188. The dispenser 180 provides storage of the requisite number (six in this example) of retainers $160_1$-$160_6$ along an enlarged diameter, proximal shaft portion of dispenser shaft 182. The diameter of the proximal shaft portion of dispenser shaft 182 exceeds the diameter of the retainer bore 162 sufficiently that the retainers $160_1$-$160_6$ are frictionally engaged and arrayed for use along the proximal shaft portion of dispenser shaft 182. Generally speaking, the distal dispenser shaft end 188 is brought into contact with the bone screw head 174 and into axial alignment with the axis of the bone screw 170 to enable dispensing of an annular retainer $160_1$-$160_6$ onto a bone screw neck 178.

The dispenser shaft distal end 188 is shaped to mate with the bone screw head 174 such that the dispenser shaft axis can be substantially axially aligned with the bone screw axis. In this example, the bone screw head 174 is shaped with a female bore 175 that the dispenser shaft distal end 188 fits into as shown in FIG. 7B. A distal shaft portion 186 is reduced in diameter so that the most distal of the retainers $160_1$-$160_6$ along the enlarged diameter, proximal shaft portion of dispenser shaft 182 can be moved from its storage point distally over the dispenser shaft 182 and then over the bone screw head 174 and onto the screw neck 178 as shown in FIG. 7B.

It will be understood that the dispenser shaft distal end 188 may alternatively be shaped to engage the external driver configuration of the bone screw head 154 of bone screw 150, whereby the female bore 175 is not necessary.

It should also be noted that a bone screw suture or suture pair may optionally extend from the bone screw heads 54, 154, 174 to facilitate screwing it into the descending pubic rami 24, 26 employing conventionally available, battery powered, bone screwdrivers. The suture is convenient for use holding the screw head to the bone screwdriver while the bone screw is being screwed into the descending pubic ramus. It is also helpful to provide the bone sutures, as shown in FIG. 1, extended through the urethral sling 30 to position it with respect to the bone screws prior to application of a retainer. The sutures may be tied off and trimmed after adequate tension is achieved and with fewer knots to provide redundancy, reduce suturing time, and minimize the remaining suture knot bulk. At the discretion of the surgeon, the suture length may be trimmed away entirely or tied with a simple knot and trimmed to minimize the size of the knot.

Figure 8A:
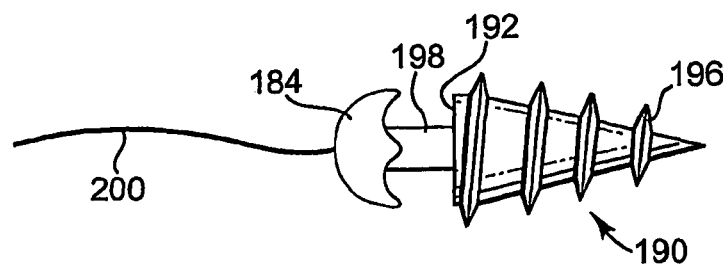
FIG. 8A is a side view of a bone screw of FIG. 6A modified to have a suture extending from the bone screw head.
Figure 8B:
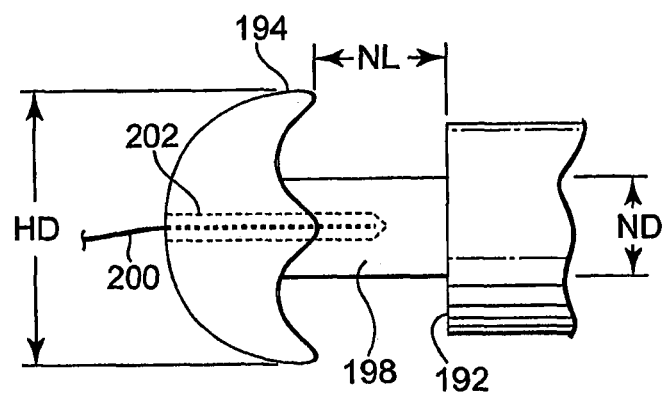
FIG. 8B is an enlarged partial side view of the mesh engaging head and neck of the bone screw of FIG. 8A.
Figure 8C:
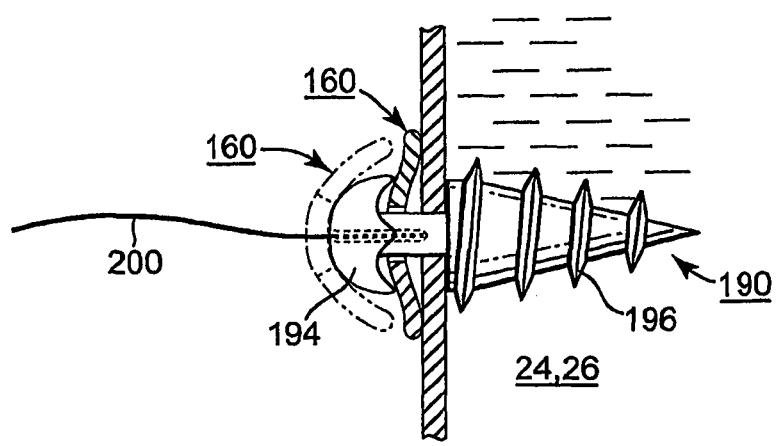
FIG. 8C is a plan view in partial section of the bone screw of FIG. 8A engaging the mesh of the urethral sling of FIGS. 2 and 3 and the sling retainer of FIG. 6C fitted over the suture and then over the bone screw head to bear against the mesh of the urethral sling of FIGS. 2 and 3 to enhance retention of the mesh to the pubic bone.

Thus, a bone screw 190 substantially corresponding to bone screw 150 but including a proximally extending suture 200 (a single suture or suture pair) and adapted to be employed with or without a retainer 160 or 164, is depicted in FIGS. 8A-8C. The bone screw 190 is generally configured like the bone screw 150 of FIGS. 6A-6G having a generally conical shaft or screw body 192 extending between a proximal screw head 194 to a distal screw tip, and a spiral screw thread 196 extends along the generally conical screw body 192 to the distal screw tip. The screw head 194 has an external driver configuration similar to that of screw head 54 to mate with a manual or powered screwdriver (not shown) that is employed to rotate and screw the bone screw 190 into bone.

In the depicted embodiment, the suture 200 is intended to be extended proximally through a hollow shaft of the battery-powered screwdriver known in the art so that suture can be used to guide the driver head into engagement with the screw head 194 so that it can rotated and does not entangle the suture 200. As shown in FIG. 8B, the proximal end of the suture 200 is entrapped in a bore 202 of the bone screw head 194. Fixation of a urethral sling 30 onto a plurality of the bone screws 190 is accomplished in any of the ways described above. It will be appreciated that bone screw 190 may be used to affix a urethral sling 30 without a retainer 160 of 164 in the manner of the bone screw 50 as described above or may be used with a retainer 160 or 164 in the manner described above.

For example, as shown in FIG. BC, the suture 200 extends proximally and the annular retainer 160 is advanced over the suture 200, then over the screw head 194 and onto the screw neck 198. The suture 200 extending proximally from the proximal screw head 190 is adapted to be threaded through a mesh pore 40 or hole made through the urethral sling 30 in any of the manners described above, and the suture 200 and screw head 194 are extended through the sling mesh pore 40 or prepared hole. Sling tension testing may proceed and repositioning may occur until satisfactory sling tension is achieved. The resilient annular retainer 160 is then moved distally over the suture 200 and fitted by expansion of the retainer bore 162 to snap over the proximal screw head 194 and against the urethral sling 30 entrapped by the screw neck 198.

Again, it will be appreciated that a kit may be provided including sets of the resilient annular retainers 160 and/or 164 that the surgeon may selectively employ as described above. It will be appreciated that the fixation of the resilient annular retainer 160 over the screw head 194 or a slotted annular retainer 164 over the screw neck 198 may be facilitated through the use of a dispenser rather than attempting to simply manually placing and pressing the retainer 160 or 164 onto the screw neck 198.

Advantageously, the kit may be incorporated into a conventional or non-conventional powered screwdriver of the type described in the above-referenced patents to screw the bone screw 190 of FIG. 8A or 150 of FIG. 6B into pubic bone. Thus, for example, a kit comprising a retainer dispenser, e.g., a powered screwdriver 300 and at least one retainer 160 may be provided as depicted in FIGS. 9A-9C and may be employed to screw the bone screw 190 of FIG. 8A or 150 of FIG. 6B into pubic bone of the descending pubic rami 24, 26 and to dispense and apply the retainer 160 against the mesh of the urethral sling 30 of FIGS. 2 and 3 to enhance retention of the mesh to the pubic bone.

As shown in FIGS. 9A and 9B, the screwdriver 300 comprises a drive motor and battery within proximal handle 302, a rotatable drive shaft 304 coupled to the drive motor, an on/off switch 310 for selectively powering the drive motor, and a stationary sheath 308 extending over the drive shaft 304. When assembled as shown in FIG. 9B, the distal screwdriver tip 306 is exposed from the distal end of the stationary sheath 308. The distal screwdriver tip 306 is shaped to mate with the external surface of the bone screw head 194 (or 154) as shown in FIG. 9C to rotate and screw the screw threads of the bone screw 190 into the ramus 24, 26 when the on/off button 310 is pushed "ON". Optionally, a shaft lumen extends continuously and proximally through the distal screwdriver tip 306, the drive shaft 304, the drive motor in handle 302, and through an opening in handle 302 to accommodate the suture 200 while the bone screw 190 is rotated and screwed into the ramus 24, 26.

In this embodiment, a set of retainers, e.g., the retainers $160_1$-$160_6$ of FIG. 7A can be retained and stored on the stationary sheath 308 and the set or a single retainer is represented by retainer 160 in FIGS. 9A-9C. As shown in FIG. 9C, the most distal retainer 160 shown in broken lines can be advanced distally from its storage position over the sheath 308 and the distal screwdriver tip 306 and dispensed into the screw neck and against the mesh of the urethral sling 30 to enhance retention of the mesh to the pubic bone of ramus 24, 26.

Figure 10A:
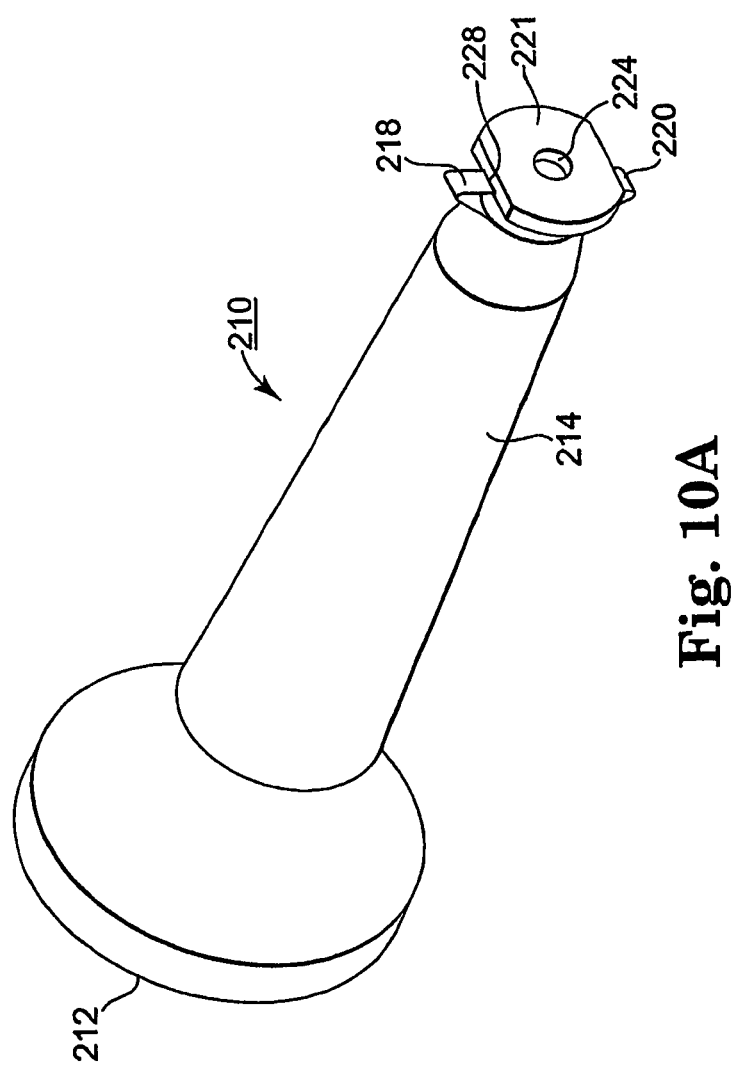
FIG. 10A is a perspective view of a further embodiment of a disposable tool coupled to a sling retainer adapted to be employed in applying the sling retainer over the suture and then over the bone screw head of the bone screw of FIG. 8A or over the bone screw head of the bone screw of FIG. 6B to bear against the mesh of the urethral sling of FIGS. 2 and 3 to enhance retention of the mesh to the pubic bone.
Figure 10B:
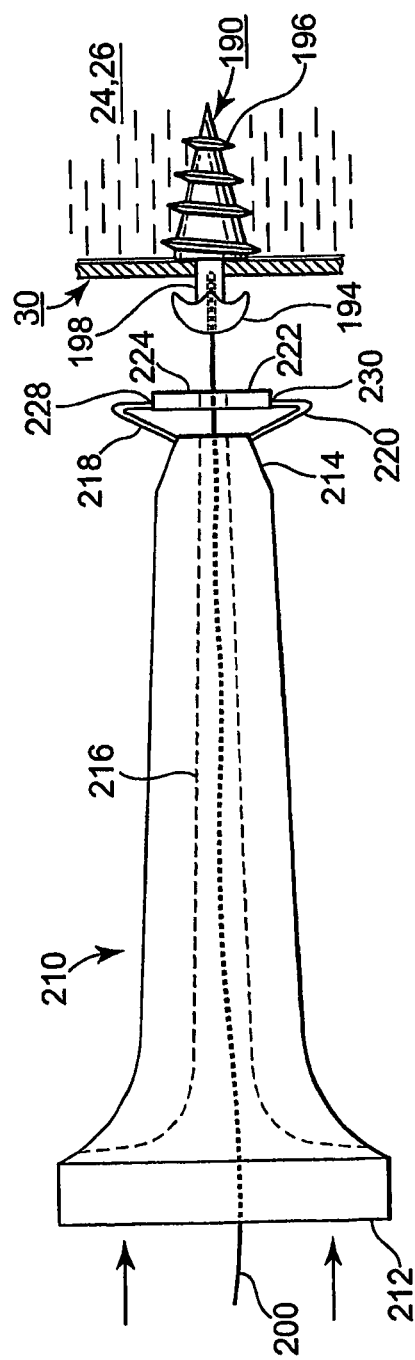
FIG. 10B is a plan view in partial cross-section of the disposable tool of FIG. 10A coupled to a sling retainer and positioned to apply the sling retainer over the suture and then over the bone screw head of the bone screw of FIG. 8A or over the bone screw head of the bone screw of FIG. 6B to bear against the mesh of the urethral sling of FIGS. 2 and 3 to enhance retention of the mesh to the pubic bone.

A further retainer dispenser 210 is depicted in FIGS. 10A and 10B that incorporates a breakaway sling retainer 222 (similar to sling retainer 160) that is attached to the dispenser 210 until the sling retainer 222 is fitted onto the bone screw neck 198 and is dispensed by a twisting motion separating the retainer 222 from the dispenser 210. The retainer dispenser 210 can be employed to fit sling retainer 222 over a bone screw head 194 of the bone screw 190 depicted in FIGS. 10A and 10B. Alternatively, the retainer dispenser 210 can be employed to fit sling retainer 222 over a bone screw head 124, 154 or 174 of the bone screws 100, 150 or 170.

The dispenser 210 comprises an elongated hollow dispenser shaft having a shaft axis and extending between a dispenser shaft proximal end 212 and a dispenser shaft distal end 214. In this embodiment, an internal dispenser lumen 216 extends between the dispenser shaft proximal and distal ends 212 and 214 to accommodate the suture 200 extending from bone screw 190. A pair of resilient suspension arms 218 and 220 extend outwardly and distally of the dispenser shaft distal end 214. The sling retainer 222 is generally annular having a central retainer bore 224 and is affixed by weak breakaway zones 228 and 230 to the respective suspension arms 218 and 220. The diameter of the retainer bore 224 is selected to be substantially equal to or slightly larger than neck diameter ND of the bone screw 190 and less than the diameter of the screw head 194. The sling retainer 222 is suspended substantially transverse to the shaft axis, and the retainer bore 224 may optionally be aligned with the shaft axis.

In use, the suture 200 is extended through the retainer bore 224 and proximally through the dispenser lumen 216. The dispenser 220 is manually grasped and advanced distally over the suture 200 until the retainer 222 abuts the screw head 194. The dispenser 220 is manipulated to advance and dilate the retainer bore 224 over the screw head 194 and onto the screw neck 198. Then, the dispenser shaft distal end 214 is manually bent and twisted to break the breakaway zones 228 and 230 and free the retainer 222. The retainer 222 then bears against the mesh of the urethral sling 30 to enhance retention of the mesh to the pubic bone of descending pubic rami 24, 26.

Figure 11A:
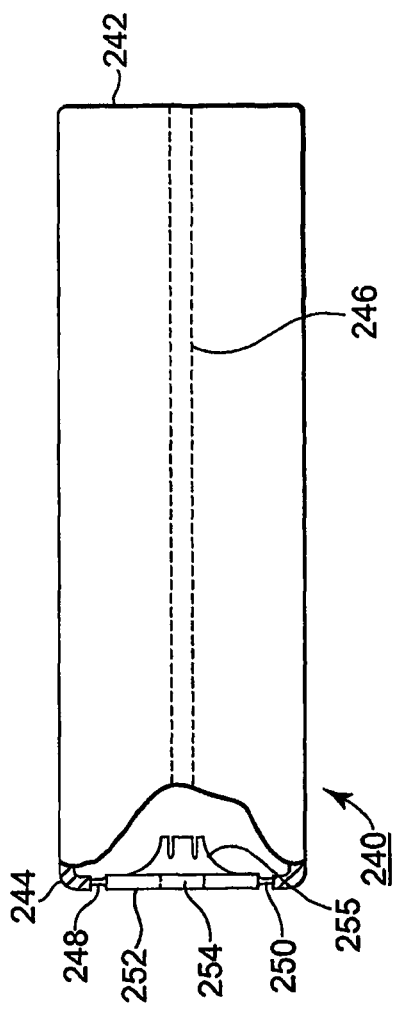
FIG. 11A is a side view of a further embodiment of a disposable tool coupled to a sling retainer adapted to be employed in applying the sling retainer over the suture and then over the bone screw head of a further embodiment of a bone screw to bear against the mesh of the urethral sling of FIGS. 2 and 3 to enhance retention of the mesh to the pubic bone.
Figure 11B:
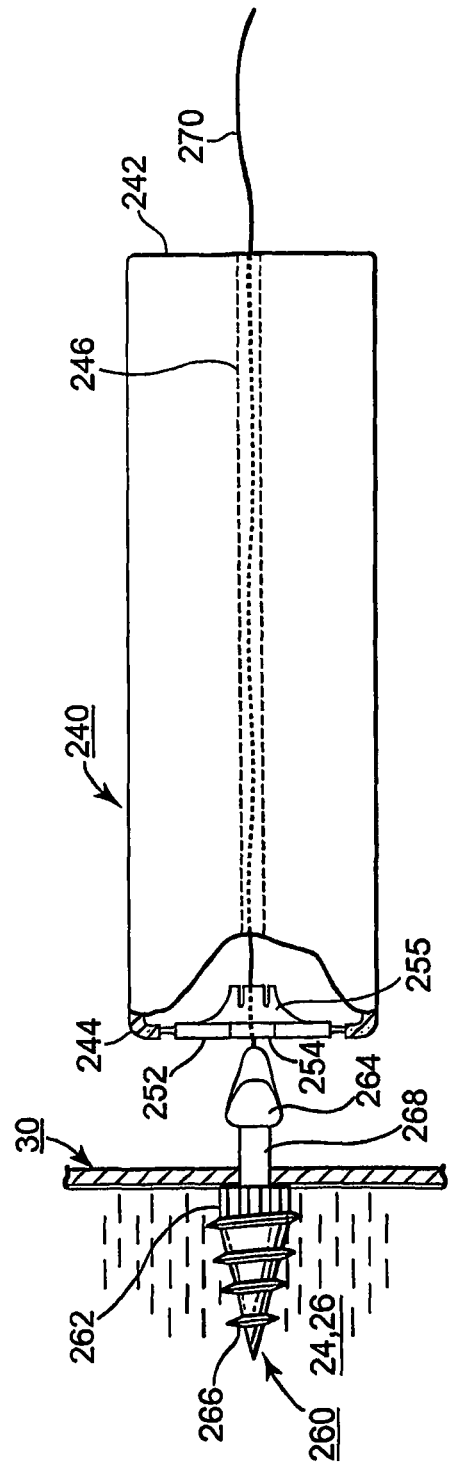
FIG. 11B is a plan view in partial cross-section of the disposable tool of FIG. 11A coupled to a sling retainer and positioned to apply the sling retainer over the suture and then over the bone screw head of the further embodiment of a bone screw to bear against the mesh of the urethral sling of FIGS. 2 and 3 to enhance retention of the mesh to the pubic bone.

A still further embodiment of a bone anchor, particularly a modified bone screw 260, is depicted in FIGS. 11A and 11B that may be used with or without a retainer dispenser, e.g. the retainer dispensers 210 and 300, or with a further retainer dispenser 240 depicted in FIGS. 11A and 11B. The retainer dispenser 240 depicted in FIGS. 11A and 11B also incorporates a breakaway retainer 252 that is retained by the dispenser 240 until it is fitted onto a bone screw neck and is dispensed by a twisting motion separating the sling retainer 252 from the dispenser 240. The retainer dispenser 240 can be employed to fit sling retainer 252 over a bone screw head 264 of the bone screw 260 as depicted in FIGS. 11A and 11B. Alternatively, the retainer dispenser 240 can be employed to fit sling retainer 252 over a bone screw head 124, 154, 174 or 194 of the bone screws 100, 150, 170 or 190.

The depicted bone screw 260 is formed with a generally conical shaft or screw body 262 extending between a proximal bone screw head 264 to a distal tip. A proximal portion of the screw body 262 has an external driver configuration to mate with the screwdriver tip of a manual or powered screwdriver (not shown) that is employed to rotate and screw the bone screw 260 into the bone. For example, the external driver configuration may be fluted or scalloped to have indentations or splines or have flats similar to a hex head that engage with female screwdriver tip shaped in a hexagonal shape or a Torx shape or the like. A spiral screw thread 266 extends along the generally conical screw body 262 between the distal screw tip and the external driver configuration. It will also be understood that the screw body 262 and the spiral screw thread 266 may take any known form employed in bone screws.

The modified bone screw 260 further has a generally conical shaped bone screw head 264 axially aligned with and coupled through a reduced diameter neck 268 with the screw body 262. A suture 270 may or may not be coupled to the bone screw head 264. The conical shaped bone screw head 264 is configured to allow advancement of a sling retainer over it and onto the screw neck 268 to engage with the mesh of the urethral sling 30 to enhance retention of the mesh to the pubic bone of descending pubic rami 24, 26.

The dispenser 240 comprises an elongated hollow dispenser shaft having a shaft axis and extending between a dispenser shaft proximal end 242 and a dispenser shaft distal end 244. In this embodiment, an internal dispenser lumen 246 extends between the dispenser shaft proximal and distal ends 242 and 244 to accommodate the suture 270 extending from bone screw 260 or the suture 200 extending from the bone screw 190. A pair of resilient suspension arms 248 and 250 extend inwardly into the shaft lumen at the and distally of the shaft distal end 244. The shaft lumen 246 extending proximally through the dispenser 260 accommodates the suture 200 extending from the bone screw head 268.

The sling retainer 252 is suspended substantially transverse to the shaft axis, and the retainer bore 224 may optionally be aligned with the shaft axis. In this embodiment, the sling retainer 252 is generally annular having a central retainer bore 254 and is affixed to the dispenser shaft distal end 244 by relatively weak breakaway zones of the respective suspension arms 248 and 250. In the depicted embodiment of retainer 252, the central retainer bore 254 is defined by expandable annular flaps 255 that are bounded by radial slits. The diameter of the retainer bore 254 is selected, when the flaps 255 are in the depicted relaxed state, to be substantially equal to or slightly larger than neck diameter of the bone screw neck 268 and less than the diameter of the screw head 264. The flaps 255 can deflect outward as the retainer 252 is pressed over the generally conical bone screw head 264 to thereby expand the diameter of the retainer bore 254 so that the bone screw head 264 can pass through the retainer bore 254.

In use, the suture 270 is extended through the retainer bore 254 and proximally through the dispenser lumen 246. The dispenser 240 is manually grasped and advanced distally over the suture 270 until the retainer 252 abuts the screw head 264. The dispenser 240 is manipulated to advance and dilate the retainer bore 254 over the screw head 264 and onto the screw neck 268. Then, the dispenser shaft distal end is manually bent and twisted to break the breakaway zones of the resilient suspension arms 248 and 250 and free the retainer 252. The retainer 252 then bears against the mesh of the urethral sling 30 to enhance retention of the mesh to the pubic bone of descending pubic rami 24, 26.

From the depiction of the retainer 252, it will be understood that the retainer 160 of FIGS. 6A-6C may be configured to have slits extending away from the retainer bore 162 to form flaps that ease expansion of the retainer bore 162 upon application over the various embodiments of bone screw heads.

The above-described bone anchor embodiments illustrated in FIGS. 4-11 have a bone screw head that extends laterally away from the bone screw neck generally through 360° rotation about the axis of the bone screw shaft or body. The anchor heads 54, 154, 174, and 194 extend laterally from the anchor body axis to a plurality of head lobes providing a head dimension (HD) exceeding the anchor neck dimension (ND). The head lobes are spaced from one another through a 360° rotation about the axis of the anchor body providing sling engaging points and a driver engagement element adapted to be engaged to drive the bone fixation mechanism into bone.

The sling retainer bores are dimensioned to fit over the bone screw head to engage the bone screw neck or to be extended laterally around the bone screw neck to fit between the bone screw head and the urethral sling. It will be understood that the present invention may be practiced employing bone anchors having bone anchor heads that do not necessarily extend laterally away from the bone screw neck by a generally through 360° rotation about the axis of the bone screw shaft or body. Alternative configurations of the bone screw heads and the sling retainers are illustrated by the following embodiments.

A further embodiment of a bone screw 320 and a sling retainer 335 adapted to engage and retain the mesh of the urethral sling 30 of FIGS. 2 and 3 is depicted in FIGS. 12A-12E. The bone screw 320 is formed with a generally conical shaft or screw body 326 extending between a proximal bone screw head 330 to a distal tip. A spiral screw thread 326 extends along the generally conical screw body between the distal screw tip and the external driver configuration or element 322. It will also be understood that the screw body and the spiral screw thread 326 may take any known form employed in bone screws.

A proximal portion or shoulder of the screw body has an external driver configuration or element 322 to mate with the screwdriver tip of a manual or powered screwdriver (not shown) that is employed to rotate and screw the bone screw 320 into the bone. For example, the external driver configuration or element 322 may be fluted or scalloped to have indentations or splines or flats similar to a hex wrench. A female screwdriver tip shaped in a complementary hexagonal shape or a Torx shape or the like can be applied over the bone screw head 330 to engage the external driver configuration.

The bone screw head 330 is generally ring-shaped and is coupled through a reduced diameter neck 328 with the screw body. The ring-shaped bone screw head 330 is configured with a laterally or transversely extending head bore 332 to receive a sling retainer, e.g., the H-shaped retainer 335 shown in FIGS. 12B and 12C or the C-shaped retainer 345 shown in FIGS. 12D and 12E.

Figure 12E:
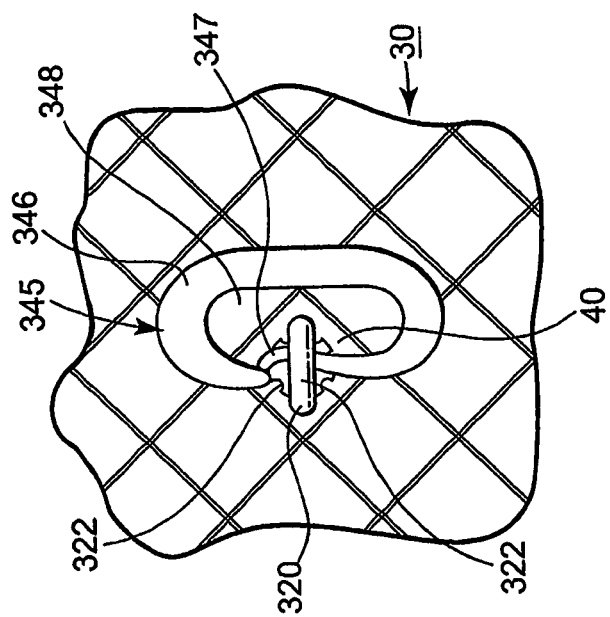
FIG. 12E is an end view of the bone screw of FIG. 12A engaging and retaining the mesh of the urethral sling of FIGS. 2 and 3 to pubic bone through the use of the spring clip, sling retainer inserted through a transverse bore of the bone screw head.

In use, the bone screw 320 is affixed to the distal screwdriver tip, via the external driver element 322 of the screw body, of a manual or battery powered screwdriver, and the spiral thread 326 is screwed into the pubic bone of a descending pubic ramus 24, 26 at a location as depicted in FIG. 1, for example, leaving the ring-shaped bone screw head 330 exposed. The urethral sling 30 is applied against the ring-shaped bone screw head 330 so that it extends through a mesh pore 40 as shown in FIGS. 12C and 12E. It will be understood that the strands surrounding the mesh pore 40 may be stretched to accommodate passage of the ring-shaped bone screw head 330 through the mesh pore 40.

The H-shaped retainer 335 depicted in FIGS. 12B and 12C is formed of a generally resilient, bio-compatible material that has an elongated retainer body 336 joined at one body end to arms 338 and 340 and at the other body end to arms 342 and 344. At least the arms 342 and 344 or one of the arms 342 or 344 can be bent into generally parallel alignment with the retainer body 336 as shown in FIG. 12B, for example, to be inserted through the transversely extending head bore 332. The H-shape of retainer 335 is restored when the arms 342 and/or 344 are released so that the arms 338, 340, 342 and 344 to extend against the strands forming the mesh of the urethral sling 30. The H-shaped retainer 335 thereby bears against the mesh of the urethral sling 30 to enhance retention of the mesh to the pubic bone of descending pubic rami 24, 26.

Figure 12D:
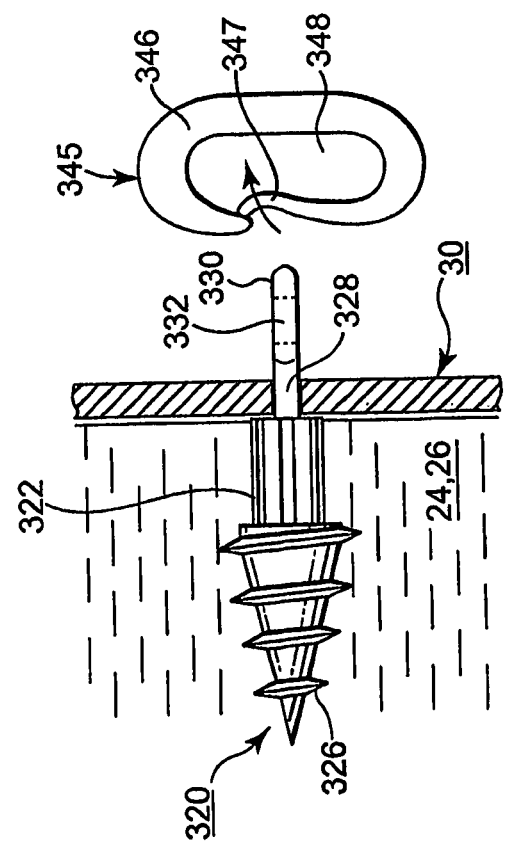
FIG. 12D is a plan view in partial section of the bone screw of FIG. 12A engaging and retaining the mesh of the urethral sling of FIGS. 2 and 3 to pubic bone through the use of a spring clip, sling retainer.

The C-shaped retainer 345 depicted in FIGS. 12D and 12E is formed of a generally resilient, bio-compatible material that has a C-shaped retainer body 346 joined at a fixed body end to an arm fixed end of a resilient arm 347 that has an arm free end extending toward the body free end of retainer body 346. The retainer body 346 and arm 347 bound a retainer bore 348. The resilient arm 347 can be bent along its length into retainer bore 348 to separate the arm free end from the retainer body free end by a gap sufficient to pass the ring-shaped bone screw head 330 therethrough. The depicted shape of the retainer arm 347 is then restored coupling the C-shaped retainer 345 to the bone screw 320. Thus, the C-shaped retainer 345 may be affixed to the bone screw 320 to extend through the bone screw head bore 332 as shown in FIG. 12E and entrap the urethral sling 30 between the ring-shaped bone screw head 330 and the exterior surface of the pubic bone. The C-shaped retainer 345 thereby bears against the mesh of the urethral sling 30 to enhance retention of the mesh to the pubic bone of descending pubic rami 24, 26.

The H-shaped retainer 335 and the C-shaped retainer 345 that extend laterally to the axis of the bone screw 320 when affixed as shown in FIGS. 12C and 12E are dimensioned in length to exceed the dimension of the sling opening, e.g., the sling pore 40, and to entrap and engage the urethral sling 30.

It will be understood that any of the above-described sling retainers may be substituted for the H-shaped retainer 335 or the C-shaped retainer 345. For example, sling retainer 164 depicted in FIGS. 6E-6G may be inserted laterally as depicted in FIG. 6F between the bone screw head 330 engage the neck 328 and to bear against the urethral sling 30 in the manner depicted in FIG. 6G. Alternatively, a sling retainer 160 depicted in FIGS. 6B-6D may be inserted over the bone screw head 330 to engage the bone screw neck 328 and to bear against the urethral sling 30 in the manner depicted in FIG. 6D. Or the sling retainer dispensers 180 (FIGS. 7A-7B), 210 (FIGS. 10A-10B), 240 (FIGS. 11A-11B) or 300 (FIGS. 9A-9c) may be employed to apply a respective sling retainer $160_1$-$160_6$, 222, 252, 160 in engagement about the bone screw neck 328.

Figure 13A:
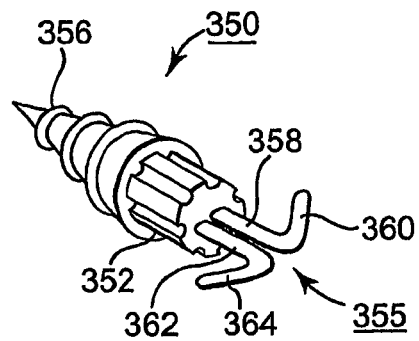
FIG. 13A is a perspective view of a further embodiment of a bone screw formed with a bone screw head adapted to be passed through a mesh port to engage and retain the mesh of the urethral sling of FIGS. 2 and 3 with or without a sling retainer interposed between the bone screw head and the urethral sling.
Figure 13B:
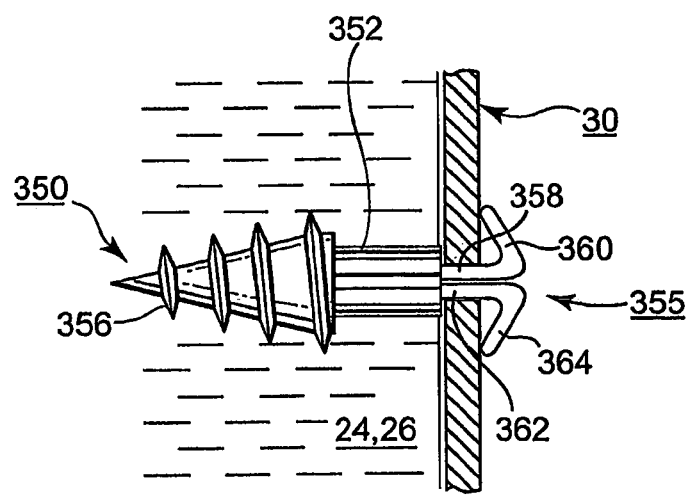
FIG. 13B is a plan view in partial section of the bone screw of FIG. 13A engaging and retaining the mesh of the urethral sling of FIGS. 2 and 3 to pubic bone through the application of at least one laterally extending tine, prong or hook of the bone screw head bearing against the urethral sling.

A still further embodiment of a bone screw 350 formed with a bone screw head 355 adapted to engage and retain the mesh of the urethral sling 30 of FIGS. 2 and 3 with or without a sling retainer is depicted in FIGS. 13A and 13B. The bone screw 350 is formed with a generally conical shaft or screw body extending between a proximal bone screw head 355 to a distal tip. A spiral screw thread 356 extends along the generally conical screw body between the distal screw tip and the external driver configuration. It will also be understood that the screw body and the spiral screw thread 356 may take any known form employed in bone screws. A proximal portion of the screw body has an external driver configuration or element 352 to mate with the screwdriver tip of a manual or powered screwdriver (not shown) that is employed to rotate and screw the bone screw 350 into the bone as described above with respect to FIGS. 12A-12E.

The modified bone screw 350 further has a generally hook-shaped bone screw head 355 that may be formed of at least one hook comprising a hook shaft and one laterally extending tine, barb or hook, wherein the lateral extension is at an angle other than transverse or 90° to the anchor body axis. In this depicted embodiment, the bone screw head 355 comprises a first hook shaft 358 and hook 360 and a second hook shaft 362 and hook 364. The hook shafts and hooks may be formed of a biocompatible metal or plastic material where the hook shaft distal ends are entrapped or otherwise fixed within or to the screw body 358. The hook shafts 358 and 362 jointly function as a bone screw neck, and the hooks 360 and 364 function as the bone screw head 355. It will be understood that the bone screw head 355 may comprise only one or more than two such hooks extending laterally from a single or plural hook shafts.

In use, the bone screw 350 is affixed to the distal screw-driver tip, via the external driver configuration or element 352 of the screw body, of a manual or battery powered screw-driver, and the spiral thread 356 is screwed into the pubic bone of a descending pubic ramus 24, 26 at a location as depicted in FIG. 1, for example, leaving the hook shafts and hooks exposed. The urethral sling 30 is applied against the hooks and hooks so that they extend through the same or separate mesh pores 40 as shown in FIG. 13B. It will be understood that the strands surrounding the mesh pore 40 may be stretched to accommodate passage of the hooks 360 and 364 forming bone screw head 355 through the mesh pore 40.

As illustrated, the strands of the mesh of the urethral sling 30 are caught beneath the laterally extending hooks 360, 364 and bear against the shafts 358 and 362, particularly as tension is applied laterally to the strands. The bone screw head 355 thereby engages with the mesh of the urethral sling 30 to enhance retention of the mesh to the pubic bone of descending pubic rami 24, 26.

It will be understood that a sling retainer, e.g., sling retainer 164 depicted in FIGS. 6E-6G may be inserted laterally as depicted in FIG. 6F between the laterally extending hooks 360, 364 to engage the shafts 358 and 362 and to bear against the urethral sling 30 in the manner depicted in FIG. 6G. Alternatively, a sling retainer 160 depicted in FIGS. 6B-6D may be inserted over the laterally extending hooks 360, 364 to engage the shafts 358 and 362 and to bear against the urethral sling 30 in the manner depicted in FIG. 6D. Or the sling retainer dispensers 180 (FIGS. 7A-7B), 210 (FIGS. 10A-10B), 240 (FIGS. 11A-11B) or 300 (FIGS. 9A-9C) may be employed to apply a respective sling retainer $160_1$-$160_6$, 222, 252, 160 in engagement about the bone screw neck comprising the shafts 358 and 362.

Figure 14A:
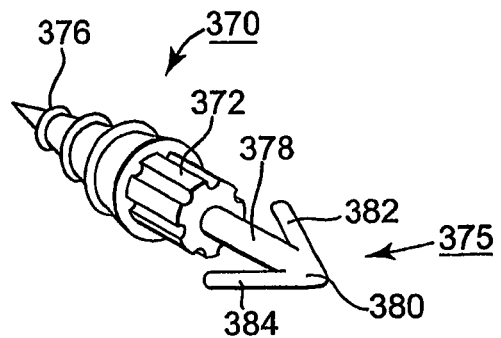
FIG. 14A is a perspective view of a further embodiment of a bone screw formed with a bone screw head adapted to engage and retain the mesh of the urethral sling of FIGS. 2 and 3 with or without a sling retainer interposed between the bone screw head and the urethral sling.
Figure 14B:
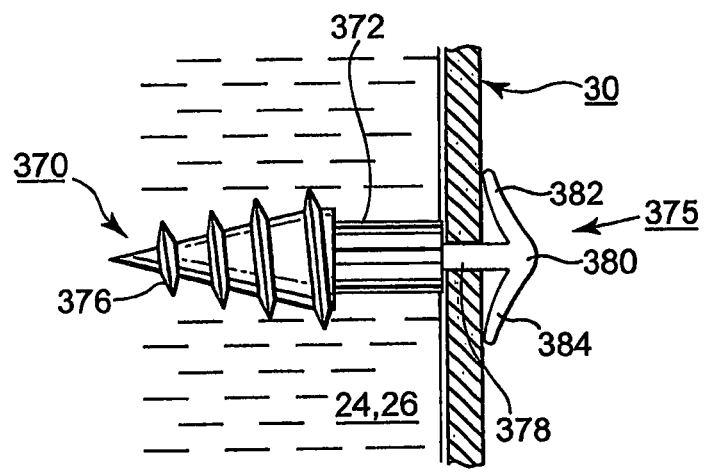
FIG. 14B is a plan view in partial section of the bone screw of FIG. 14A engaging and retaining the mesh of the urethral sling of FIGS. 2 and 3 to pubic bone through the use of bilaterally extending tines, prongs or hooks of the bone screw head bearing against the urethral sling.

Yet another embodiment of a bone screw 370 formed with a bone screw head 375 adapted to engage and retain the mesh of the urethral sling 30 of FIGS. 2 and 3 with or without the use of a sling retainer is depicted in FIGS. 14A and 14B. The bone screw 370 is formed with a generally conical shaft or screw body extending between a proximal bone screw head 375 to a distal tip. A spiral screw thread 376 extends along the generally conical screw body between the distal screw tip and the external driver configuration. It will also be understood that the screw body and the spiral screw thread 376 may take any known form employed in bone screws. A proximal portion of the screw body has an external driver configuration or element 372 to mate with the screwdriver tip of a manual or powered screwdriver (not shown) that is employed to rotate and screw the bone screw 370 into the bone in the manner described above with respect to FIGS. 12A-12E.

A bone screw neck 378 extends proximally and substantially axially from the bone screw body to a free end 380. The modified bone screw 370 further has a generally T-shaped or arrow-shaped bone screw head 375 that is formed at the proximal, free end 380 of the bone screw neck 378. Laterally and generally distally extending tines or barbs or hooks 382 and 384 extend from free end 380 to engage the strands of the mesh of the urethral sling 30. The bone screw neck 378 and the hooks 382 and 384 may be formed integrally at free end 380 and of a biocompatible metal or plastic material where the distal end of the neck 378 is entrapped or otherwise fixed within or to the screw body.

In use, the bone screw 370 is affixed to the distal screwdriver tip, via the external driver configuration or element 372 of the screw body, of a manual or battery powered screwdriver, and the spiral thread 376 is screwed into the pubic bone of a descending pubic ramus 24, 26 at a location as depicted in FIG. 1, for example, leaving the neck 378 and hooks 382, 384 exposed. The urethral sling 30 is applied against the bone screw head 375 so that it extends through a mesh pore 40 so that the urethral sling 30 is disposed between the laterally extending hooks 382, 384 and the surface of the pubic bone as shown in FIG. 14B. It will be understood that the strands surrounding the mesh pore 40 may be stretched to accommodate passage of the bone screw head 375 through the mesh pore 40.

The strands of the mesh of the urethral sling 30 are then caught beneath the laterally extending hooks 382, 384 and bearing against the neck 378, particularly as tension is applied laterally to the strands. The bone screw head 375 thereby engages with the mesh of the urethral sling 30 to enhance retention of the mesh to the pubic bone of descending pubic rami 24, 26.

It will be understood that a sling retainer, e.g., sling retainer 164 depicted in FIGS. 6E-6G may be inserted laterally as depicted in FIG. 6F between the laterally extending hooks 382, 384 to engage the neck 378 and to bear against the urethral sling 30 in the manner depicted in FIG. 6G. Alternatively, a sling retainer 160 depicted in FIGS. 6B-6D may be inserted over the laterally extending hooks 382, 384 to engage the bone screw neck 378 and to bear against the urethral sling 30 in the manner depicted in FIG. 6D. Or the sling retainer dispensers 180 (FIGS. 7A-7B), 210 (FIGS. 10A-10B), 240 (FIGS. 11A-11B) or 300 (FIGS. 9A-9c) may be employed to apply a respective sling retainer $160_1$-$160_6$, 222, 252, 160 in engagement about the bone screw neck 378.

Figure 15A:
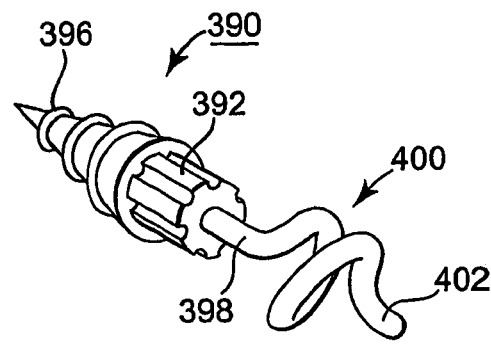
FIG. 15A is a perspective view of a further embodiment of a bone screw formed with a bone screw head with a spiral extension adapted to engage and retain the mesh of the urethral sling of FIGS. 2 and 3 without a sling retainer interposed between the bone screw head and the urethral sling.
Figure 15B:
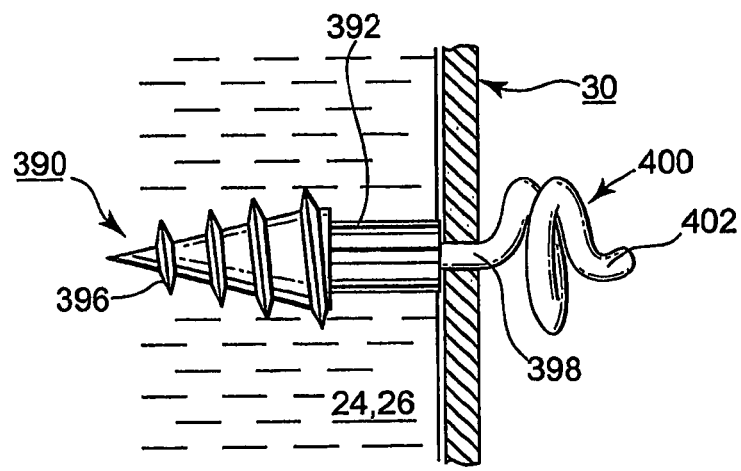
FIG. 15B is a plan view in partial section of the bone screw of FIG. 14A engaging and retaining the mesh of the urethral sling of FIGS. 2 and 3 to pubic bone through the use of the spiral extension of the bone screw head bearing against the urethral sling.

Still another embodiment of a bone screw 390 formed with a bone screw spiral head 400 adapted to engage and retain the mesh of the urethral sling 30 of FIGS. 2 and 3 with or without a sling retainer is depicted in FIGS. 15A and 15B. The bone screw 390 is formed with a generally conical shaft or screw body 392 extending between a proximal bone screw head 375 to a distal tip. A spiral screw thread 396 extends along the generally conical screw body 392 between the distal screw tip and the external driver configuration. It will also be understood that the screw body 392 and the spiral screw thread 396 may take any known form employed in bone screws. A proximal portion of the screw body 392 has an external driver configuration to mate with the screwdriver tip of a manual or powered screwdriver (not shown) that is employed to rotate and screw the bone screw 390 into the bone in the manner described above with respect to FIGS. 12A-12E.

A bone screw neck 398 extends proximally and substantially axially from the bone screw body 392. The modified bone screw 390 further has a generally spiral-shaped bone screw head 400 that is formed at the proximal, free end of the bone screw neck 398. A laterally and generally distally extending spiral 402 of at least one turn extends from the end of the bone screw neck 398 to a spiral free end. The spiral 400 functions as a spiral catch engaging the strands of the mesh of the urethral sling 30. The bone screw neck 398 and the spiral 402 may be formed integrally and of a biocompatible metal or plastic material where the distal end of the neck 398 is entrapped or otherwise fixed within or to the screw body 392.

In use, the bone screw 390 is affixed to the distal screwdriver tip, via the external driver configuration of the screw body 392, of a manual or battery powered screwdriver, and the spiral thread 396 is screwed into the pubic bone of a descending pubic ramus 24, 26 at a location as depicted in FIG. 1, for example, leaving the neck 398 and spiral 402 exposed. The urethral sling 30 is applied against the bone screw head 400 so that the spiral 402 extends through a mesh pore 40 and the urethral sling 30 is disposed between the laterally extending turn(s) of the spiral 402 and the surface of the pubic bone as shown in FIG. 15B. It will be understood that the strands surrounding the mesh pore 40 may be stretched to accommodate passage of the spiral 402 through the mesh pore 40.

The strands of the mesh of the urethral sling 30 are then caught beneath the laterally extending spiral turn(s) of spiral 402 and bearing against the neck 398, particularly as tension is applied laterally to the strands. The bone screw head 400 thereby engages with the mesh of the urethral sling 30 to enhance retention of the mesh to the pubic bone of descending pubic rami 24, 26.

It will be understood that a sling retainer, e.g., sling retainer 164 depicted in FIGS. 6E-6G may be inserted laterally as depicted in FIG. 6F between the laterally extending turn(s) of the spiral 402 to engage the neck 398 and to bear against the urethral sling 30 in the manner depicted in FIG. 6G. Alternatively, the free end of the spiral 402 may be inserted through the retainer bore 163 of the sling retainer 160 depicted in FIGS. 6B-6D so that the sling retainer 160 may be advanced over the laterally extending turn(s) of the spiral 402 to engage the neck 398 and to bear against the urethral sling 30 in the manner depicted in FIG. 6D.

The invention claimed is:

1. A surgical kit comprising:

a urethral sling having opposed sling sides and extending between a first sling end adapted to be coupled to a first pubic bone and a second sling end adapted to be coupled to a second pubic bone to fix the urethral sling in a sub-urethral location to support the urethra and alleviate incontinence, the urethral sling having or capable of having a sling opening formed through the sling adjacent the first and second sling ends;

at least one bone anchor comprising an anchor body having an anchor body axis and extending between a distal bone fixation mechanism adapted to be attached to pubic bone through an anchor neck having a neck dimension lateral to the anchor body axis to a proximal anchor head having a head dimension lateral to the anchor body axis exceeding the neck dimension, whereby the urethral sling is adapted to be applied against the anchor head to insert the anchor head through the sling opening and engage the sling with the anchor neck;

at least one sling retainer having a retainer dimension exceeding the head dimension adapted to be engaged by one of the anchor head and the anchor neck and applied against the urethral sling, the sling retainer comprising a retainer bore having a dimension smaller than the head dimension, the retainer comprising an elastic material and being capable of being stretched to pass the retainer bore over the anchor head to allow the sling retainer to be interposed between the urethral sling and the anchor head to retain the sling attached to the bone anchor; and a sling retainer dispenser comprising:

an elongated dispenser a shaft axis and extending from a shaft proximal end to a shaft distal end, the shaft distal end engageable with the bone anchor head for axial alignment of the shaft axis with the anchor body axis; and the at least one sling retainer supported along a length of the dispenser shaft with the retainer bore axially aligned with the shaft axis,
wherein the at least one sling retainer is distally moveable along the shaft from the shaft distal end and over the bone anchor head engaged by the shaft distal end.

2. The surgical kit of claim 1, wherein the retainer bore extends through the sling retainer and has a bore dimension selected with respect to the head dimension to enable advancement of the sling retainer over the anchor head into engagement with a portion of the urethral sling.

3. The surgical kit of claim 2, wherein the sling retainer is formed of a resilient material enabling expansion of the retainer bore sufficiently to pass over the anchor head when axially advanced over the anchor head, and slits are formed extending away from the retainer bore toward a peripheral edge of the sling retainer to form flaps that facilitate expansion of the retainer bore as the sling retainer is passed over the anchor head.

4. The surgical kit of claim 2, wherein the anchor head comprises a driver engagement element adapted to be engaged to drive the bone fixation mechanism into bone and further comprising an anchor driver that engages the driver engagement element to drive the bone fixation mechanism into bone.

5. The surgical kit of claim 4, wherein the anchor driver further comprises:
a drive motor adapted to be manually grasped;
an elongated drive shaft having a shaft axis and extending from a shaft proximal end coupled to the drive motor and a drive shaft distal end shaped to engage the bone anchor head to enable axial alignment of the shaft axis with the bone anchor axis, the drive motor adapted to drive the drive shaft and impart bone penetrating force to the bone fixation mechanism; and
the sling retainer dispenser, which is supported by the drive shaft that in turn supports the at least one sling retainer to be applied over the anchor head engaged by the drive shaft distal end.

6. The surgical kit of claim 5, wherein:
the sling retainer dispenser further comprises:
an elongated dispenser sheath having a sheath axis and sheath lumen extending between a sheath proximal end and a sheath distal end;
and the at least one sling retainer supported along the length of the dispenser shaft with the retainer bore axially aligned with the shaft axis; and
the drive shaft is extended through the sheath lumen, whereby the at least one sling retainer supported along the length of the dispenser shaft may be moved distally along the sheath and from the drive shaft distal end over the bone anchor head engaged by the shaft distal end.

7. The surgical kit of claim 6, wherein:
the elongated drive shaft comprises a shaft lumen; and
the bone anchor further comprises a suture extending from the anchor head adapted to be extended through the shaft lumen to facilitate engagement of the drive shaft distal end with the driver engagement element.

8. The surgical kit of claim 7, wherein the sling retainer further comprises a slot extending from a retainer body edge to the retainer bore dimensioned to receive the anchor neck and enable lateral advancement of the sling retainer with respect to the anchor neck to dispose the anchor neck in the retainer bore and to dispose the sling retainer between the sling and the anchor head.

9. The surgical kit claim 1, wherein the at least one anchor head extends laterally to the anchor neck at a generally constant dimension exceeding the anchor neck dimension through 360° rotation about the axis of the anchor body, and the at least one sling retainer bore is dimensioned to fit over the anchor head to engage the anchor neck or to be extended laterally around the anchor neck to fit between the anchor head and the urethral sling.

10. The surgical kit of claim 1, wherein the anchor head comprises at least one hook extending substantially laterally away from the anchor neck and the anchor body axis a dimension exceeding the lateral dimension of the anchor neck.

11. The surgical kit of claim 1, wherein the anchor head comprises a spiral wire having at least one spiral turn extending substantially laterally to the anchor neck and the anchor body axis a dimension exceeding the lateral dimension of the anchor neck.

12. A sling retention apparatus in combination with a sling retainer dispenser for securing a urethral sling at a plurality of locations to pubic bone to fix the urethral sling in a sub-urethral location to support the urethra and alleviate incontinence, the urethral sling having a sling opening, wherein the sling retention apparatus comprises:
at least one bone anchor adapted to be attached to pubic bone, the at least one bone anchor comprising an anchor neck, an anchor head having a head dimension enabling passage through the sling opening, and an anchor body axis, and
at least one sling retainer having a retainer dimension exceeding the head dimension and a neck receiving port, the neck receiving port having a dimension smaller than the head dimension, the retainer comprising an elastic material and being capable of being stretched to pass the receiving port over the anchor head,
wherein the urethral sling is adapted to be applied against the anchor head to insert the anchor head through the sling opening and apply the sling against the anchor neck, and the sling retainer is adapted to be interposed between the sling and the anchor head with the anchor neck extending through the neck receiving port to retain the sling against the anchor neck and to inhibit passage of the sling over the anchor head; and wherein the sling retainer dispenser comprises:
an elongated dispenser shaft having a shaft axis and extending from a shaft proximal end to a shaft distal end, the shaft distal end shaped to engage the at least one anchor head for axial alignment of the shaft axis with the anchor body axis, wherein the at least one sling retainer is supported along the length of the dispenser shaft with the neck receiving ort axially aligned with the shaft axis, and wherein the at least one sling retainer is distally moveable along the dispenser shaft from the shaft distal end and over the bone anchor head engaged by the shaft distal end.

13. The sling retention apparatus of claim 12, wherein the anchor head comprises a spiral wire having at least one spiral turn extending substantially laterally to the anchor neck and an anchor body axis a dimension exceeding the lateral dimension of the anchor neck.

14. The sling retention apparatus of claim 12 further comprising a driver engagement element adapted to be engaged to drive a bone fixation mechanism adapted to attach to pubic bone,
whereby the driver engagement element is adapted to be engaged by a driver to drive the bone anchor into bone, and the urethral sling is adapted to be applied against the anchor head to insert the anchor head through the sling opening and engage the sling with the anchor neck.

15. The sling retention apparatus of claim 14, further comprising an elongated suture affixed to the anchor head and extending to a suture free end adapted to guide a driver head into engagement with the driver engagement element.

16. The sling retention apparatus of claim 14, wherein the anchor head extends laterally from the anchor body axis to a plurality of head lobes providing a head dimension exceeding the anchor neck dimension, the head lobes spaced from one another through a 360° rotation about the axis of the anchor body providing sling engaging points and the driver engagement element adapted to be engaged to drive the bone fixation mechanism into bone.

17. The sling retention apparatus of claim 14, wherein the anchor head comprises at least one hook extending substantially laterally away from the anchor neck and the anchor body axis a dimension exceeding the lateral dimension of the anchor neck.

18. A method of securing a urethral sling at a plurality of locations to pubic bone to fix the urethral sling in a suburethral location to support the urethra and alleviate incontinence, the urethral sling having a sling opening, the method comprising:

providing a bone anchor having an anchor body with an anchor body axis and extending between a distal bone fixation mechanism adapted to be attached to pubic bone through an anchor neck having a neck dimension lateral to the anchor body axis to a proximal anchor head having a head dimension lateral to the anchor body axis exceeding the neck dimension, and a driver engagement element adapted to be engaged to drive the bone fixation mechanism into bone, providing a driver having a drive shaft and a driving element at a drive shaft distal end;

engaging the driver engagement element with the driving element;

operating the driver to drive the bone anchor into pubic bone, applying the opening of the urethral sling around the anchor neck;

providing a sling retainer having a retainer dimension exceeding the head dimension and a neck receiving bore by supporting the sling retainer on a sling retainer dispenser; and after applying the opening of the urethral sling around the anchor neck, interposing the sling retainer between the sling and the anchor head with the anchor neck extending through the neck receiving bore to retain the sling against the anchor neck and to inhibit passage of the sling over the anchor head by aligning the sling retainer dispenser with the anchor head, dispensing the sling retainer from the sling retainer dispenser between the sling and the anchor head, and moving the sling retainer over the anchor head.

19. The method of claim 18 wherein the neck receiving bore has a dimension smaller than the head dimension, the sling retainer comprising an elastic material, and the method comprises stretching the neck receiving bore of the sling retainer to pass the sling retainer over the anchor head.

* * * * *

UNITED STATES PATENT AND TRADEMARK OFFICE
CERTIFICATE OF CORRECTION

PATENT NO. : 8,864,650 B2
APPLICATION NO. : 11/993397
DATED : October 21, 2014
INVENTOR(S) : Inman et al.

It is certified that error appears in the above-identified patent and that said Letters Patent is hereby corrected as shown below:

IN THE SPECIFICATION

In Column 1, Line 50, delete "dosing" and insert -- closing --, therefor; In Column 1, Line 60, delete "dose" and insert -- close --, therefor.

In Column 10, Line 30, delete "and or/applies" and insert -- and/or applies --, therefor.

In Column 13, Line 25, delete "rami 24 and 36," and insert -- rami 24 and 26, --, therefor.

In Column 14, Lines 7-8, delete "head 110" and insert -- head 54 --, therefor; In Column 14, Line 30, delete "rami 24 and 36" and insert -- rami 24 and 26 --, therefor.

In Column 15, Lines 7-8, delete "retainer 150" and insert -- retainer 160 --, therefor.

In Column 17, Line 8, delete "FIG. BC," and insert -- FIG. 8C, --, therefor; In Column 17, Line 12, delete "screw head 190" and insert -- screw head 194 --, therefor.

In Column 18, Line 13, delete "screw head 124," and insert -- screw head 54, --, therefor;
In Column 18, Line 34, delete "dispenser 220" and insert -- dispenser 210 --, therefor; In Column 18, Line 36, delete "dispenser 220" and insert -- dispenser 210 --, therefor; and
In Column 18, Line 56, delete "screw head 124," and insert -- screw head 54, --, therefor.

In Column 19, Line 25, delete "dispenser 260" and insert -- dispenser 240 --, therefor; In Column 19, Line 26, delete "head 268." and insert -- head 264. --, therefor.

In Column 22, Line 2, delete "body 358." and insert -- body 326. --, therefor.

In Column 23, Line 60, delete "spiral 400" and insert -- spiral 402 --, therefor.

Signed and Sealed this
Fifth Day of January, 2016

Michelle K. Lee
*Director of the United States Patent and Trademark Office*

CERTIFICATE OF CORRECTION (continued)
U.S. Pat. No. 8,864,650 B2

IN THE CLAIMS

In Column 24, Line 63, in Claim 1, delete "dispenser" and insert -- dispenser shaft having --, therefor.

In Column 25, Line 66, in Claim 9, delete "kit claim" and insert -- kit of claim --, therefor.

In Column 26, Line 49, in Claim 12, delete "receiving ort" and insert -- receiving port --, therefor.